United States Patent
Chisholm et al.

(10) Patent No.: US 10,281,447 B2
(45) Date of Patent: May 7, 2019

(54) METHODS AND APPARATUS FOR COMBINING TECHNICAL AND REGULATORY INFORMATION COMPRISING THE COMPILING AND NORMALIZATION OF DISPARATE TECHNICAL, REGULATORY AND OTHER DATA

(71) Applicant: Flotek Industries, Inc., Houston, TX (US)

(72) Inventors: John Chisholm, Montgomery, TX (US); Glenn Collins, Montgomery, TX (US); Kathleen Collins, Montgomery, TX (US); Joby Hughes, Houston, TX (US)

(73) Assignee: FLOTEK INDUSTRIES, INC., Houston, TX (US)

( * ) Notice: Subject to any disclaimer, the term of this patent is extended or adjusted under 35 U.S.C. 154(b) by 415 days.

(21) Appl. No.: 14/687,763

(22) Filed: Apr. 15, 2015

(65) Prior Publication Data

US 2015/0293071 A1 Oct. 15, 2015

Related U.S. Application Data

(60) Provisional application No. 61/979,970, filed on Apr. 15, 2014.

(51) Int. Cl.
*G06Q 10/06* (2012.01)
*G01N 33/24* (2006.01)
(Continued)

(52) U.S. Cl.
CPC ....... *G01N 33/241* (2013.01); *G01N 33/2823* (2013.01); *G06Q 10/063* (2013.01); *G06Q 10/10* (2013.01); *G06Q 10/06* (2013.01)

(58) Field of Classification Search
CPC ...... G06Q 10/10; G06Q 10/06; G06Q 10/063; E21B 44/00; E21B 47/00; E21B 49/00;
(Continued)

(56) References Cited

U.S. PATENT DOCUMENTS 7,043,486 B2 5/2006 Cope
7,096,223 B2 8/2006 Cope
(Continued)

OTHER PUBLICATIONS

International Search Report and Written Opinion issued in International Patent Application No. PCT/US15/26023, dated Jul. 28, 2015, 7 pages.

*Primary Examiner* — John E Breene
*Assistant Examiner* — Jeffrey P Aiello
(74) *Attorney, Agent, or Firm* — Davis Wright Tremaine LLP; Philip H. Albert; Heather M. Colburn

(57) ABSTRACT

A computer system presents information related to drilling operations using a computer display, the method comprising: for each of a plurality of drilling sites, obtaining chemical composition data of hydraulic fluids used in the drilling site, wherein the chemical composition data is obtained from a first data source, for each of the plurality of drilling sites, obtaining well yield data for the drilling site, wherein the well yield data is obtained from a second data source distinct from the first data source, matching the chemical composition data and the well yield data by drilling site, and displaying, on the computer display, a combination of chemical composition and well yield for the plurality of drilling sites. The matching might be based on drill site parameters, such as geographic location and/or geologic characteristics.

20 Claims, 45 Drawing Sheets

(51) Int. Cl.
*G01N 33/28* (2006.01)
*G06Q 10/10* (2012.01)

(58) Field of Classification Search
CPC .............. G06F 17/30563; G01N 33/24; G01N 33/241; Y04S 10/54
USPC ............ 175/24, 50; 702/6, 11; 707/694, 722
See application file for complete search history.

(56) References Cited

U.S. PATENT DOCUMENTS

| | | |
|---|---|---|
| 7,155,439 B2 | 12/2006 | Cope |
| 7,293,029 B2 | 11/2007 | Cope |
| 7,669,133 B2 | 2/2010 | Chikirivao et al. |
| 7,991,680 B2 | 8/2011 | Livesay et al. |
| 8,026,198 B2 * | 9/2011 | Miller ..................... C09K 8/22 |
| | | 175/65 |
| 8,171,397 B2 | 5/2012 | Chikirivao et al. |
| 8,321,313 B2 | 11/2012 | Livesay et al. |
| 8,566,194 B2 | 10/2013 | Livesay et al. |
| 9,667,468 B2 | 5/2017 | Chikirivao et al. |
| 9,742,614 B2 | 8/2017 | Chikirivao et al. |
| 9,898,462 B2 | 2/2018 | Cope |
| 2008/0208475 A1 | 8/2008 | Karr et al. |
| 2009/0225630 A1 | 9/2009 | Zheng et al. |
| 2013/0270011 A1 | 10/2013 | Akkurt et al. |
| 2014/0025413 A1 | 1/2014 | Yeager |
| 2014/0040077 A1 | 2/2014 | Livesay et al. |
| 2015/0166873 A1 * | 6/2015 | Tomlinson ............. C09K 8/487 |
| | | 166/293 |
| 2015/0198038 A1 * | 7/2015 | Bartetzko ............... E21B 49/00 |
| | | 166/250.05 |

* cited by examiner

10,034 Wells

Wells Without Oil/Bypass Service Company
All Well Types, United States, Eagle Ford Play

| Service Company | Count |
|---|---|
| Schlumberger Technology Corp | 1,587 |
| Halliburton Energy Services | 1,572 |
| Service Company N/A | 738 |
| Frac Tech Services International LLC | 677 |
| Weatherford Fracturing Technologies | 627 |
| CJ Energy Services | 606 |
| Baker Hughes Inc | 560 |
| Universal Well Services Inc | 305 |
| Bosque Systems LLC | 279 |
| Cudd Energy Services Inc | 273 |
| Trican Well Services Ltd | 234 |
| Mission Well Services | 220 |
| Sanjel Corp | 216 |

METHODS AND APPARATUS FOR COMBINING TECHNICAL AND REGULATORY INFORMATION COMPRISING THE COMPILING AND NORMALIZATION OF DISPARATE TECHNICAL, REGULATORY AND OTHER DATA

FIELD OF THE INVENTION

Methods and apparatus provide for combining technical and regulatory information comprising the compiling and normalization of disparate technical, regulatory and other data in the use of oil and gas production research, marketing, regulatory analysis, economic evaluations, and environmental and hazardous waste evaluation. Fields of use extend to other industries including health care, environmental and climate studies. Applications extend to all of the above fields as they relate to insurance underwriting and risk management, financial market analysis, and political and supply chain risk.

BACKGROUND OF THE INVENTION

Drilling and other ventures are capital intensive and risky. As a result, many have sought ways to reduce risk and provide predictability.

There is a need to improve the analysis of production of oil and gas data from disparate sources for use in research, marketing, regulatory analysis, economic evaluations, and environmental and hazardous waste evaluation, which has applications beyond oil and gas production to other regulated fields such as healthcare and application to insurance underwriting and risk management, financial market analysis, political risk and supply chain analysis.

SUMMARY OF THE INVENTION

In various embodiments, a computer system presents information related to drilling operations using a computer display, the method comprising: for each of a plurality of drilling sites, obtaining chemical composition data of hydraulic fluids used in the drilling site, wherein the chemical composition data is obtained from a first data source, for each of the plurality of drilling sites, obtaining well yield data for the drilling site, wherein the well yield data is obtained from a second data source distinct from the first data source, matching the chemical composition data and the well yield data by drilling site, and displaying, on the computer display, a combination of chemical composition and well yield for the plurality of drilling sites. The matching might be based on drill site parameters, such as geographic location and/or geologic characteristics.

The following detailed description together with the accompanying drawings will provide a better understanding of the nature and advantages of the present invention.

BRIEF DESCRIPTION OF THE DRAWING FIGURES

The figures illustrate aspects of embodiments of the present invention and it should be understood that the present invention is not limited to those embodiments.

FIG. 34 is an exemplary screen shot of a table showing wells grouped by features.

FIGS. 39-45 are a series of screen shots from an application that might be implemented.

DETAILED DESCRIPTION OF THE INVENTION

Figure 1:
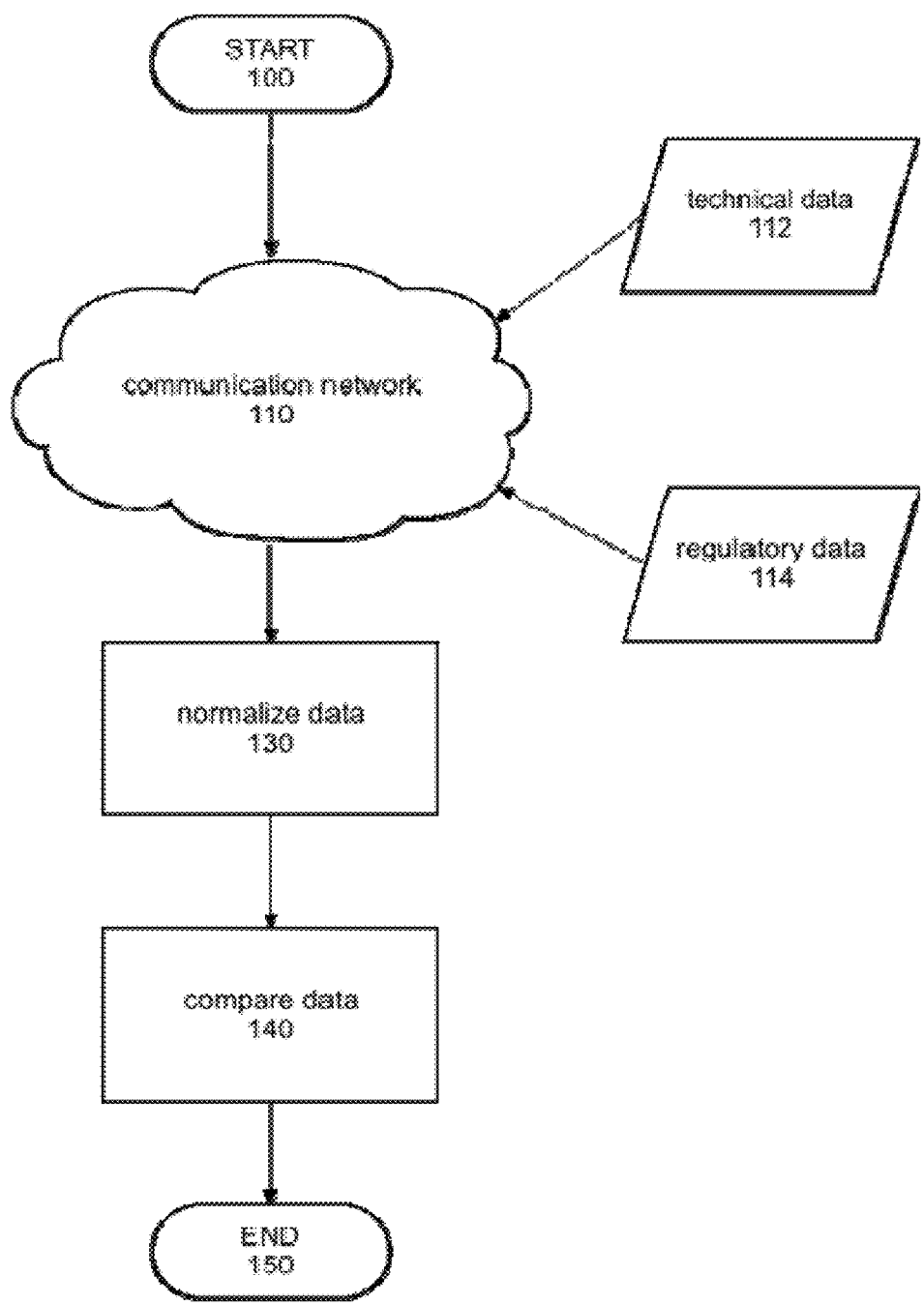
FIG. 1 is an exemplary flow diagram of the process used in a particular embodiment of the present invention to combine technical and regulatory information for oil and gas wells and aggregate data into a database for comparing data and possibly other purposes.

FIG. 1 provides an overview of a preferred embodiment of the process of the present invention. As shown, the process of the present invention obtains regulatory data via a communications network and technical data via a communications network. The regulatory data and the technical data are normalized. After normalization, the regulatory data and the technical data are combined into a single database. The single database is utilized to compare regulatory and technical data. For example, in the oil and gas industry, regulatory data, i.e., production, can be compared for oil and gas wells with specific technical data, i.e., a specific chemical. The processes, communication, and data storage can be performed using computers.

Figure 2:
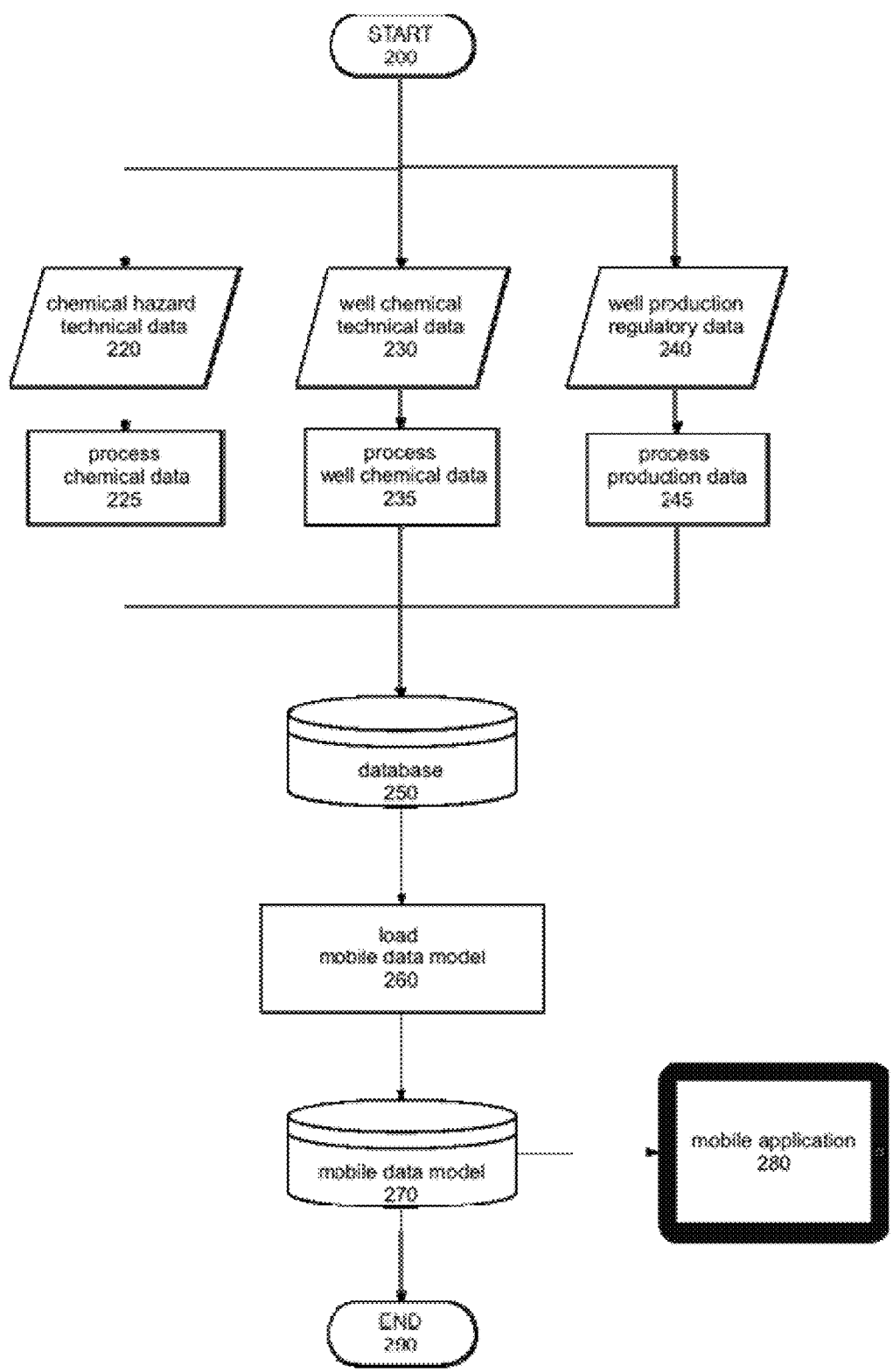
FIG. 2 is an exemplary flow diagram of the process shown in FIG. 1, wherein the process steps of combining data into an initial database and loading the mobile data model are depicted for a mobile-based embodiment of the present invention.

FIG. 2 provides an overview of a preferred embodiment of the process of the present invention wherein the database is loaded into a mobile data store for use with a mobile-based embodiment of the present invention. The mobile-based embodiment generally applies to any electronic device than is small enough to carry and enables some kind of computing. The mobile-based embodiment will allow for comparison of technical data and regulatory data. For example, in the oil and gas industry, regulatory data, i.e., production, can be compared for oil and gas wells with specific technical data, i.e., a specific chemical.

For many years, government regulatory agencies have taken in and stored data in a format well suited to the specific function and purpose of their respective statutory mandates. Oftentimes, this data is collected to support tax functions. In other respects, the statutory mandates reflect a concern for public safety and health. Yet other non-governmental agencies assemble data to further their own for-profit or not-for-profit motives.

In the oil and gas industry, for instance, state regulatory agencies routinely monitor the exploration and production of oil and gas assets. These records include not only where a given well is drilled, but how deep, in what direction or directions, and other related data. The primary purpose of these statutes and regulations is to generate and maximize tax revenues from the extraction of these minerals from the state.

In recent years, with the advent of increased drilling in the United States, horizontal drilling techniques, and advanced chemical and other applications for enhancement of recovery of oil and gas, the amount of this data has exploded. These regulations and the resulting data that is collected vary widely from state to state.

In addition, there has been a push by various groups to know more about what is being injected into the resulting wells, especially including chemicals that are used in the drilling and completion process. As a result, most oil and gas production operations, at this time mostly voluntarily, submit data regarding the chemicals that are used. The data is collected separately from the regulatory data and, with its different purpose, in different form and arranged in a largely different format than the government data related to taxation and data related to monitoring of what is actually extracted and how.

For many years, petroleum has been recovered from subterranean reservoirs using drilled wells and production equipment. Oil and natural gas are found and produced from porous and permeable subterranean formations, or reservoirs. The porosity and permeability of the formation determine its ability to store hydrocarbons, and the facility with which the hydrocarbons can be extracted from the formation. Generally, the lifecycle of an oil and/or gas well includes drilling to form a wellbore casing, cementing, stimulation, and enhanced or improved oil recovery. Various aspects of the lifecycle of an oil and/or gas well are designed to facilitate the extraction of oil and/or gas from the reservoir via the wellbore. A wide variety of fluids is utilized during the lifecycle of an oil and/or gas well. In order to improve extraction of oil and/or gas, additives have been incorporated into various fluids utilized during the lifecycle of an oil and/or gas well. The incorporation of additives into fluids utilized during the lifecycle of an oil and/or gas well can increase crude oil or formation gas, for example, by reducing capillary pressure and/or minimizing capillary end effects.

As an example, fracturing and acidizing are commonly used techniques to stimulate the production of oil and/or gas from reservoirs, wherein a stimulation fluid is injected into the wellbore and the formation (reservoir). In a typical matrix acidizing or fracturing treatment, from 1 to 15 barrels per foot to several million gallons of stimulation fluid are pumped into a reservoir (e.g., via the wellbore). The stimulation fluid can comprise additives to aid in the stimulation process, for example, proppants, scale inhibitors, friction reducers, biocides, gases such as carbon dioxide and nitrogen, acids, slow release acids, corrosion inhibitors, buffers, viscosifiers, clay swelling inhibitors, oxygen scavengers, and surfactants. Later in the life of the well additional fluids and gases may be injected into the well to remediate damage, maintain pressure or contact and recover further oil.

When selecting or using a fluid to be utilized during the lifecycle of an oil and/or gas well, it is important for the fluid to comprise the right combination of additives and components to achieve the necessary characteristics of the specific end-use application. A primary goal amongst all aspects of the lifecycle of a well is to optimize recovery of oil and/or gas from the reservoir.

However, in part because the fluids utilized during the lifecycle of an oil and/or gas well are often utilized to perform a number of tasks simultaneously, achieving necessary optimal characteristics is not always easy. Accordingly, it would be desirable if a wide variety of additives were available which could be selected to achieve the necessary characteristics and/or could be easily adapted. Furthermore, it is desirable that the additives provide multiple benefits and are useful across multiple portions of the lifecycle of the well.

For example, a challenge often encountered is fluid recovery following injection of fracturing fluids or other fluids into the wellbore. Often, large quantities of injected fluids are trapped in the formation, for example, in the area surrounding the fracture and within the fracture itself. It is theorized that the trapping of the fluid is due to interfacial tension between water and reservoir rock and/or capillary end effects in and around the vicinity of the face of the fractured rock. The presence of trapped fluids generally has a negative effect on the productivity of the well. While several approaches have been used to overcome this problem, for example, incorporation of co-solvents and/or surfactants (i.e., low surface tension fluids), there is still the need for improved additives, as well as a greater understanding as to how to select the additives to maximize the productivity of the well. The use of microemulsions is known, however, selection of an appropriate microemulsion for a particular application remains challenging, as well as there is a continued need for microemulsions with enhanced abilities. An example of such a microemulsion is the CnF® (Complex nano-Fluid®) microemulsion developed by Flotek Industries, Inc.

Although a number of additives are known in the art and used in the drilling of well and there is a plethora of data on the existing reservoirs and production of oil and gas on a state-by-state basis, and there is also a large amount of data being collected for other purposes as to what is being used in each well, there is a need to improve the analysis of production of oil and gas data from disparate sources for use in research, marketing, regulatory analysis, economic evaluations, and environmental and hazardous waste evaluation, which has applications beyond oil and gas production to other regulated fields such as healthcare and application to insurance underwriting and risk management, financial market analysis, political risk and supply chain analysis.

Figure 3:
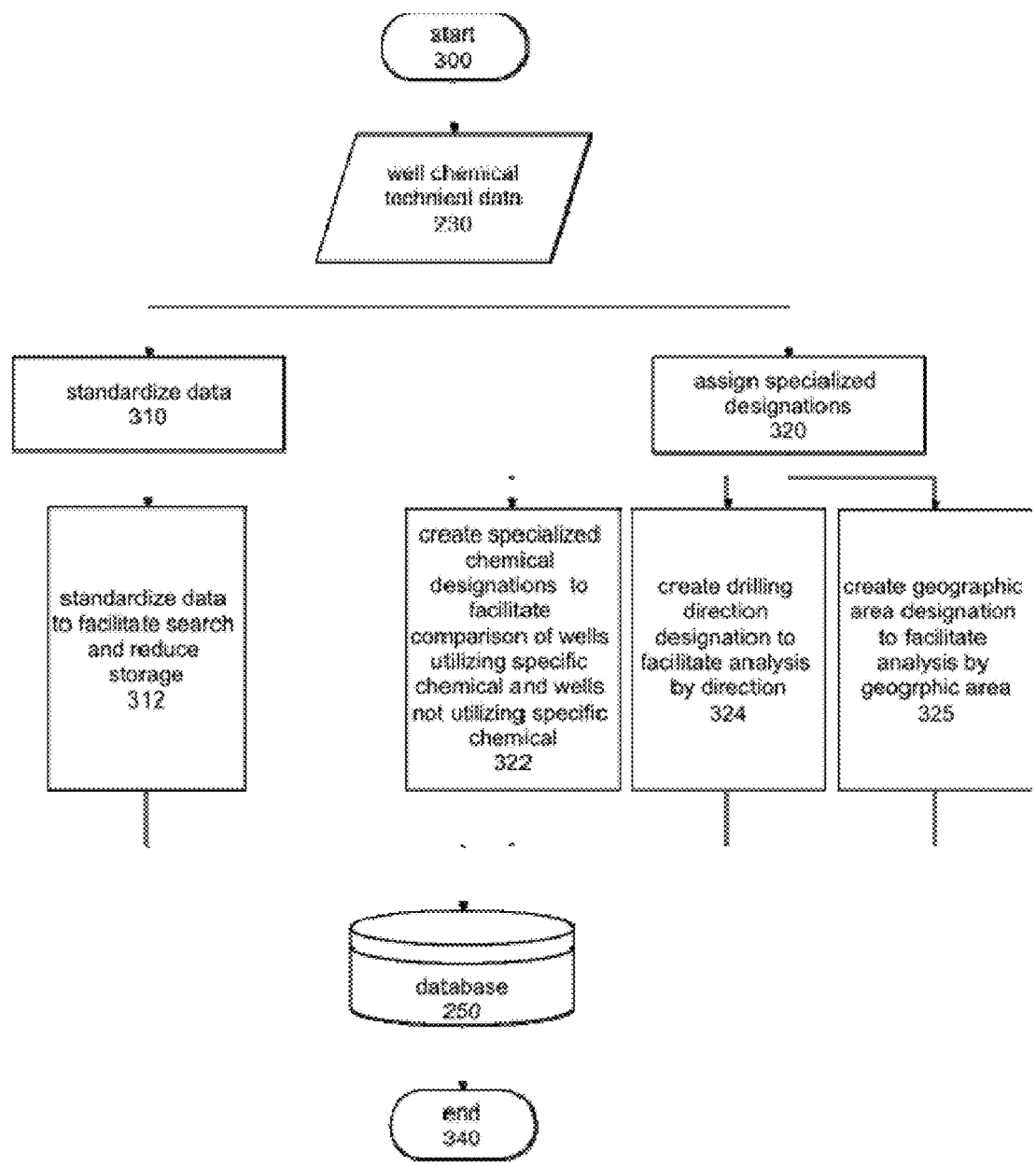
FIG. 3 is a more detailed flow diagram showing the process of FIG. 2, in finer detail, for the step of processing well chemical technical data by standardizing data and assigning specialized designations for the particular embodiment of the present invention.

FIG. 3 provides an overview for the process for standardizing and assigning specialized designations for the well chemical technical data. In certain embodiments, the well chemical technical data must be standardized and have specialized designations assigned for the purpose of the invention. The well chemical technical data is added to the combined database (Block 250) upon completion of processing.

In those certain embodiments, data must be standardized to allow for searches and filtering. As an example, Company Alpha and Beta may be listed as Company Alpha and Beta for several wells, and then as Company Alpha & Beta for several wells. This is standardized to one spelling for filter and search purposes. The same general reasoning applies to standardizing all fields utilized for filter and search.

Specialized designations are assigned to facilitate filter, search, and data comparison. Designations assigned might be (1) drilling direction, (2) basin in which the well is located, (3) shale play in which the well is located, and (4) specialized chemical designations. These designations allow for filter and search by designation and provide the capability to compare wells by designation.

For example, wells could be filtered for Company Alpha and Beta located in a certain basin. A specific chemical designation for comparison can be selected, for example, the chemical designation of "CnF®" to refer to the CnF® additive. Then regulatory data can be compared for Company Alpha and Beta with and without "CnF®", by drilling direction. In various places herein, "CnF®" might refer to the CnF® additive-based microemulsion developed by Flotek Industries, Inc., but it should be apparent that many of the techniques here might find applicability with other materials and other fields of use.

Figure 4:
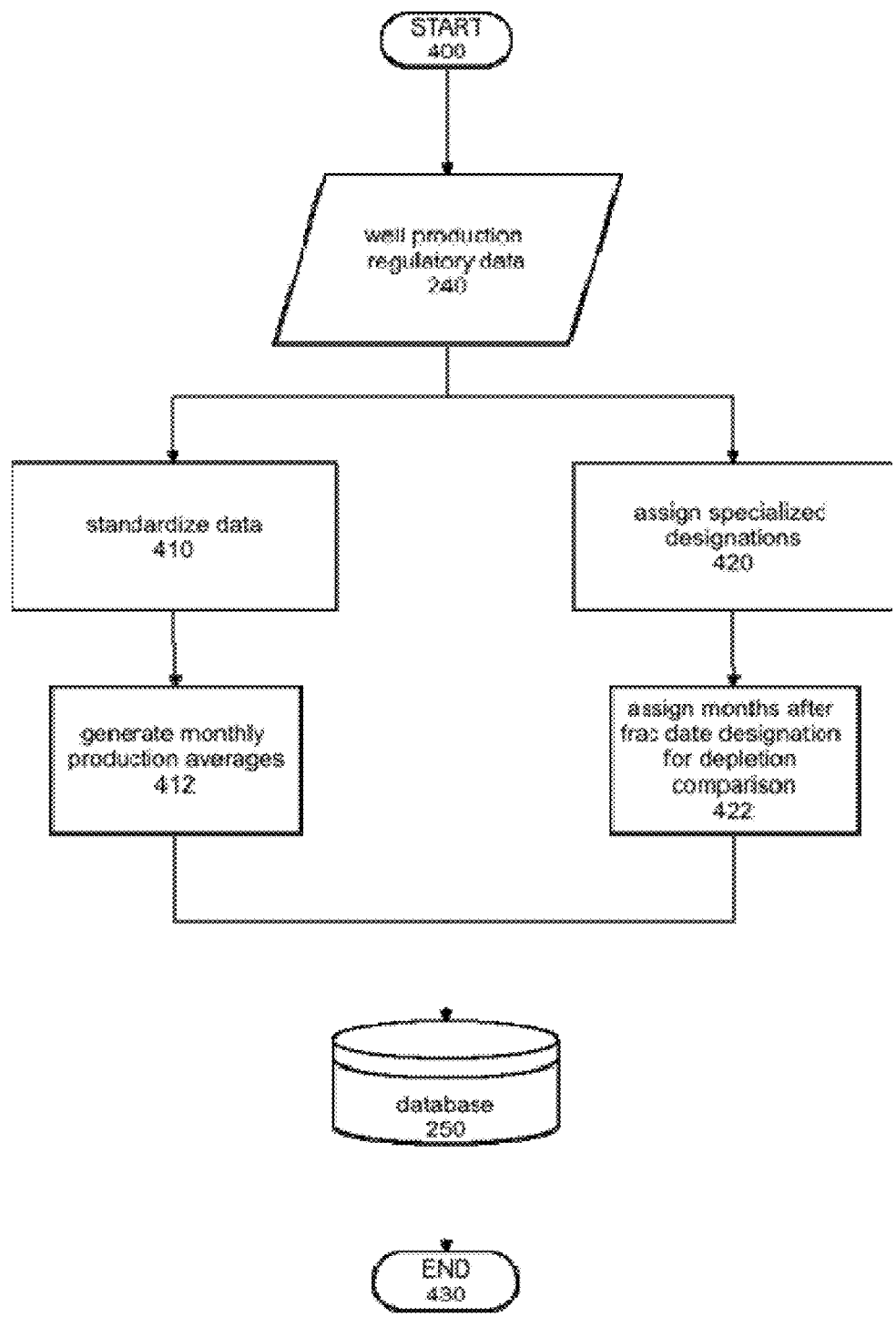
FIG. 4 is a more detailed flow diagram showing the process of FIG. 2, in finer detail, for the step of processing well production regulatory data by standardizing data and assigning specialized designations for the particular embodiment of the present invention.

FIG. 4 provides an overview for the process for the well regulatory production data. The well regulatory production data generally comes from the reporting agency for the state in which the well is located. Texas data, for example, is from the Texas Railroad Commission.

Production data must be analyzed and monthly production data must be calculated for each well. Production comparisons in the invention are based on monthly production rates.

The analysis and process to calculate monthly production may be different for each reporting agency that provides data. For example, production data from the Texas Railroad Commission is reported monthly, but production is not necessarily related on a one-to-one basis for each well. Another example is the state of Pennsylvania, for which production data is related on a one-to-one basis for each well, but production is reported on a semi-annual basis.

The well production regulatory data is added to the combined database (Block 250) upon completion of processing.

Figure 5:
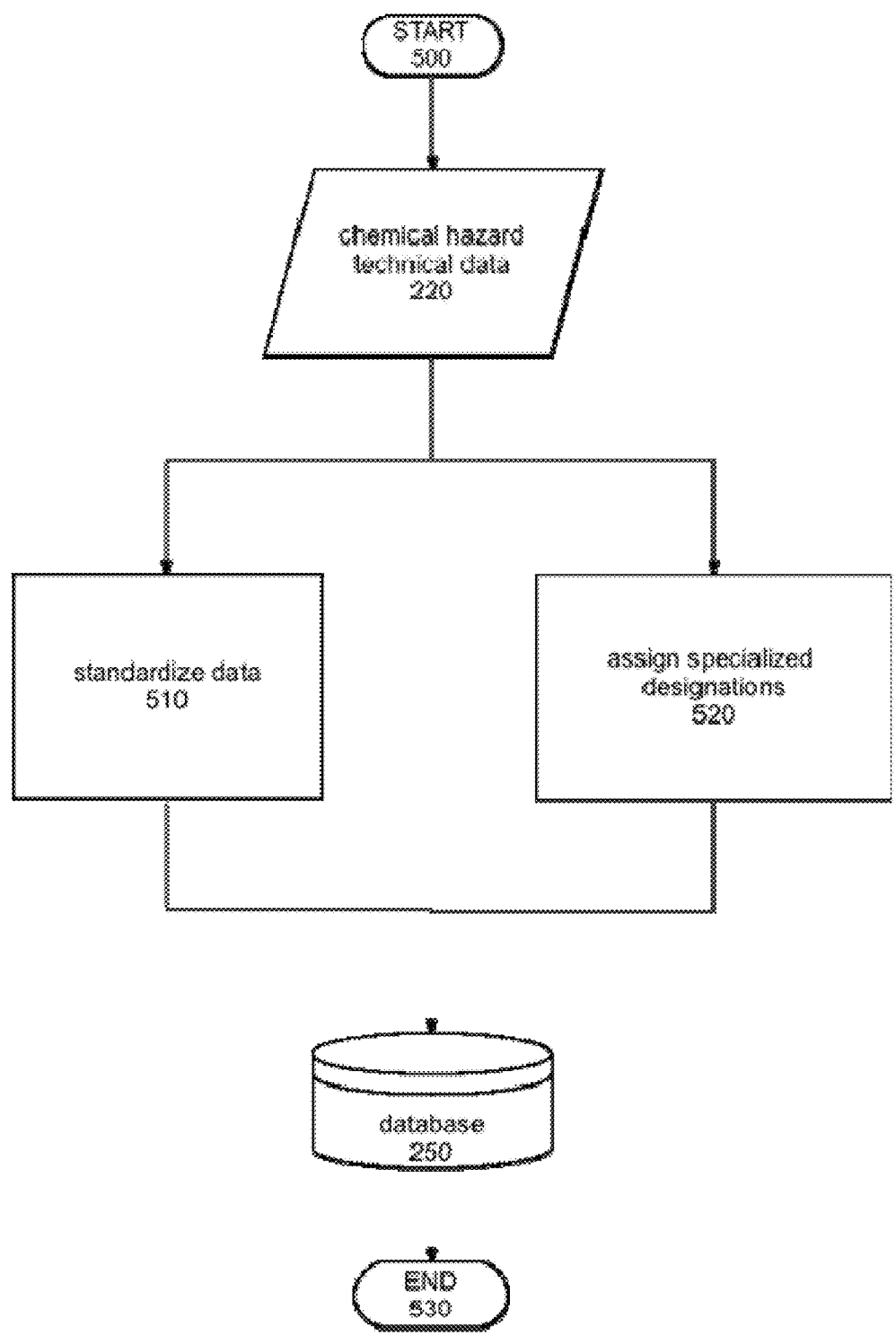
FIG. 5 is a more detailed flow diagram showing the process of FIG. 2, in finer detail, for the step of processing chemical hazard technical data by standardizing data and assigning specialized designations for the particular embodiment of the present invention.

FIG. 5 provides an overview for the process for the chemical hazard technical data. The chemical hazard technical data generally comes from the Internet and The Globally Harmonized System of Classification and Labeling. The chemical hazard technical data is standardized and specialized designations are assigned. The chemical hazard technical data is added to the combined database (Block 250) upon completion of processing.

Figure 6:
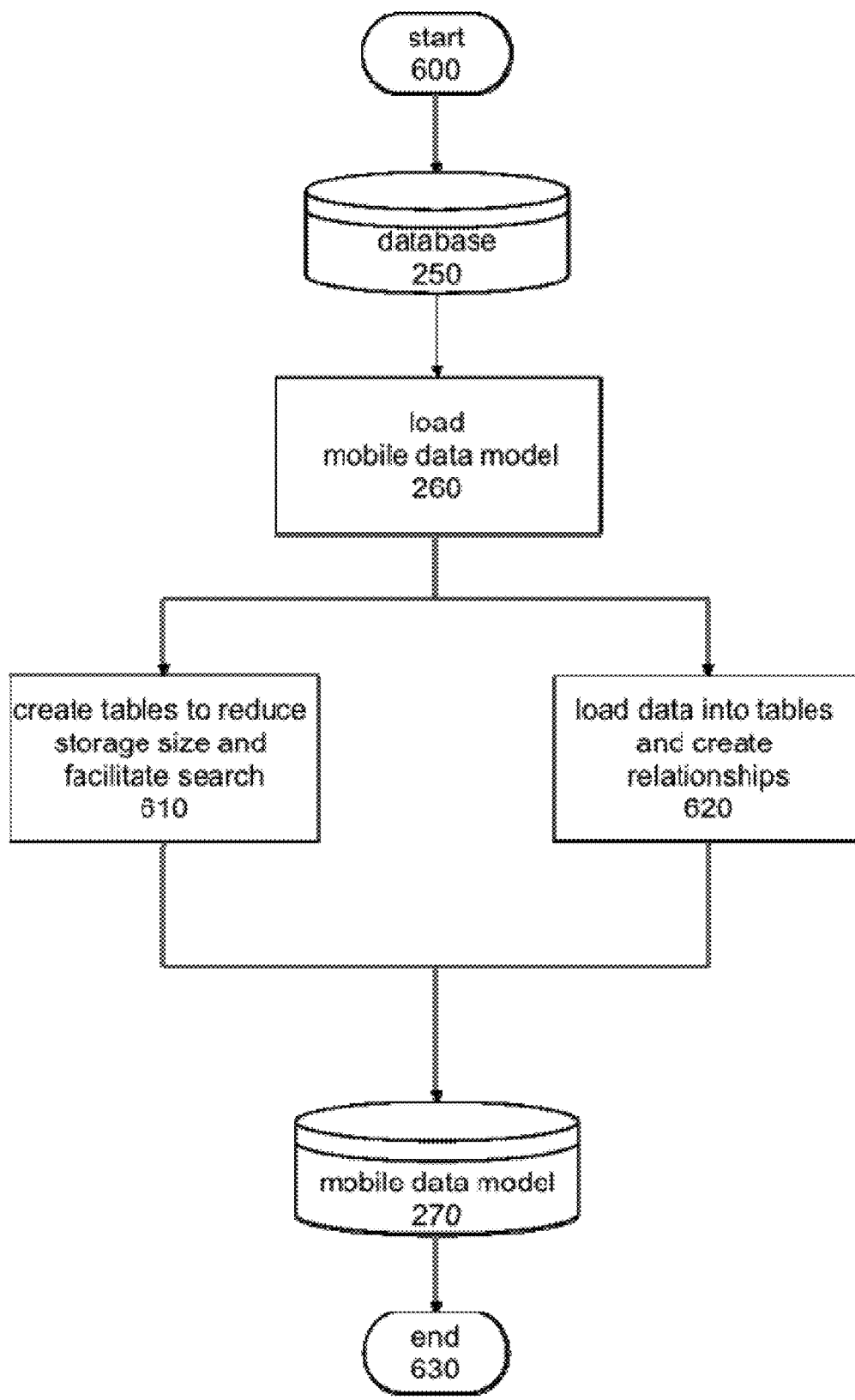
FIG. 6 is a more detailed flow diagram showing the process of FIG. 2, in finer detail, for the step of loading the mobile data model by creating tables and relationships for the particular embodiment of the present invention.

FIG. 6 provides an overview for the process for loading the mobile data model (Block 260) from the database (Block 250) created from the well chemical technical data, well production regulatory data, and chemical hazard technical information. This process might be performed by a computer system described herein. Tables are created to reduce storage size and to optimize search functions. Due to storage and memory limitations of current mobile devices, reduction of storage size might be necessary, where it may not be necessary on non-mobile databases. For example, the chemical technical data includes several million records. Lookup tables are created to reduce the storage size for the chemical technical data. For example, substituting a key for the ingredient string "N-Cocoamidopropyl-N,N-dimethyl-N-2-hydroxypropylsulfobetainE" allows the string to be stored only once, instead of potentially thousands of times.

Data is loaded into the mobile data model and relationships are created if necessary. The load process may vary slightly depending on the mobile data model platform. For example, for the iOS™ platform, if Core Data is utilized for the mobile data model, relationships must be created programmatically, as Core Data does not read relationships from another database source.

Figure 7:
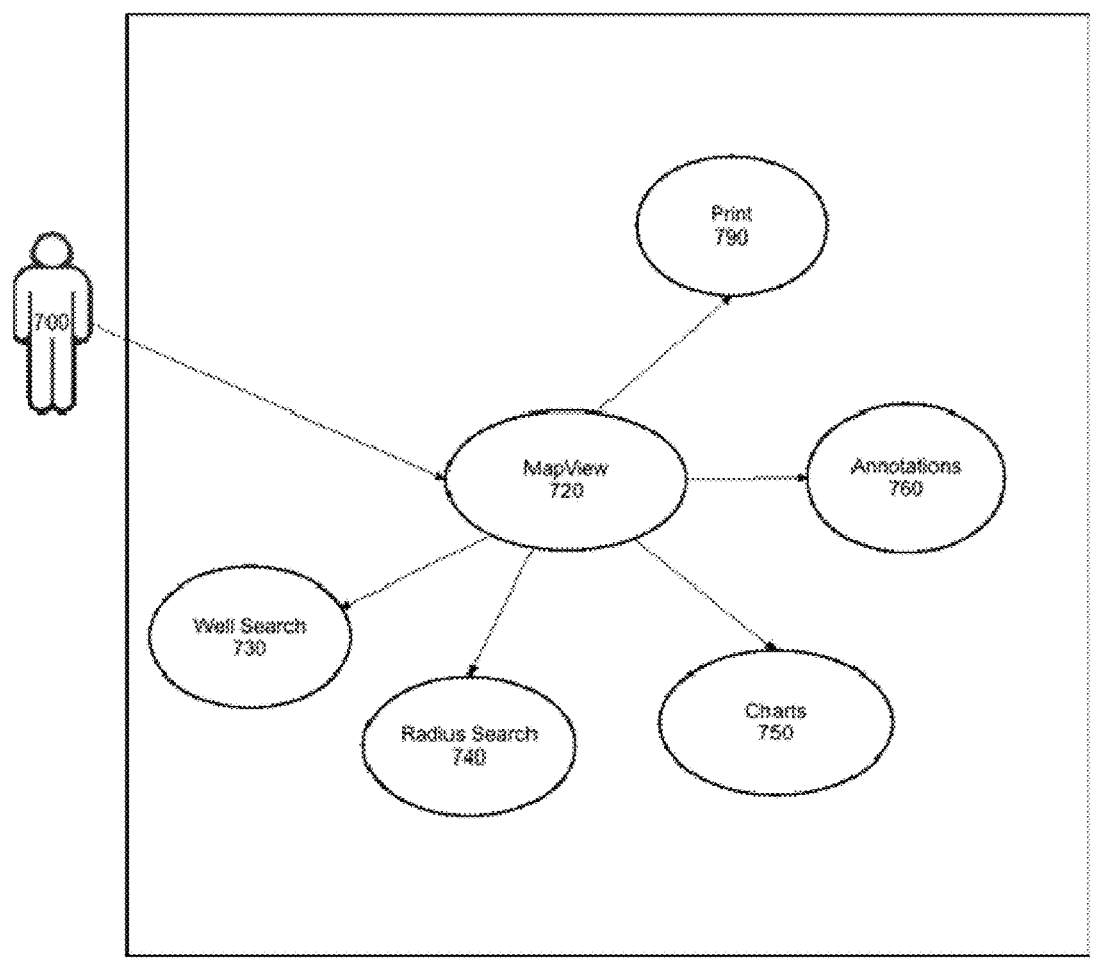
FIG. 7 represents a use case diagram depicting the major functional elements for a mobile-based embodiment of the present invention.

FIG. 7 provides a use case diagram for the invention. The use case diagram illustrates the major functions of the invention. The first function with which the user may interact is the map view. From the map view, the user may interact with one of many other functions; well search, radius search, charts, annotations, and print functions. Functions are described in greater detail in the following discussion of FIG. 8.

Figure 8:
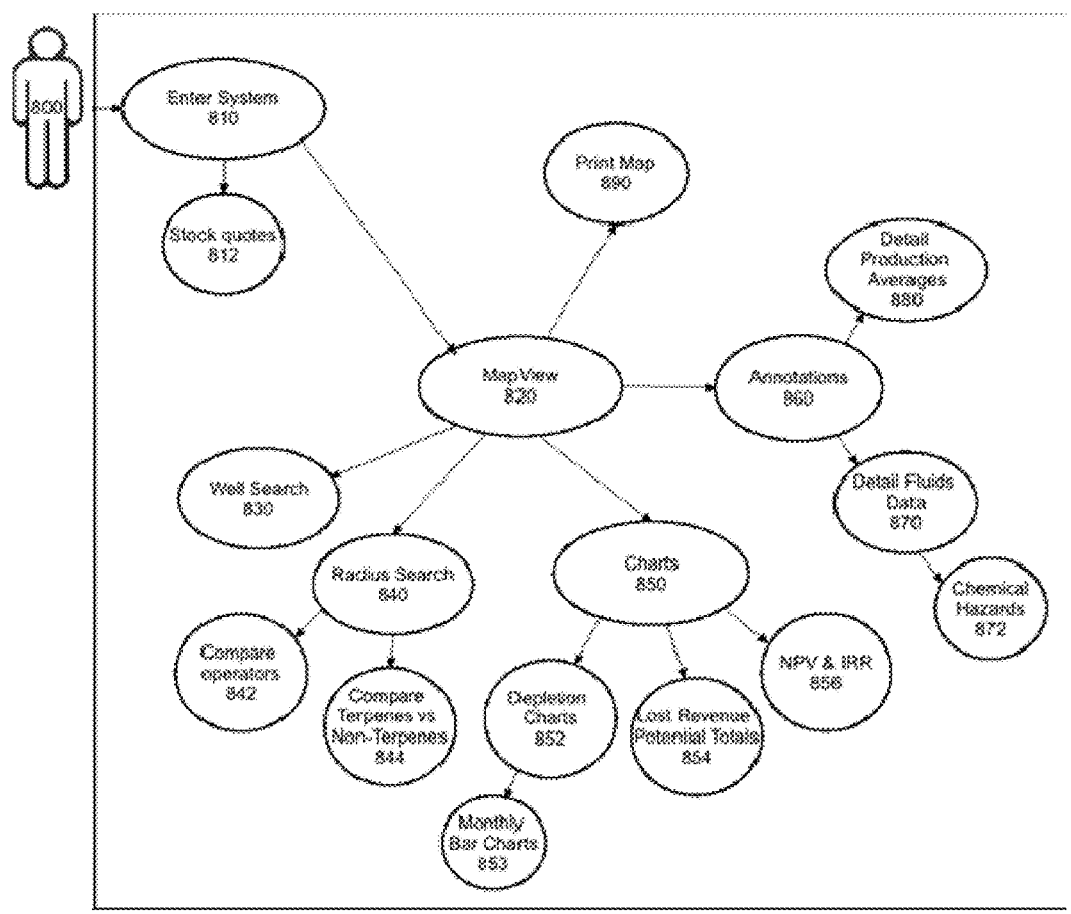
FIG. 8 represents a more detailed use case diagram depicting the major functional elements and sub-elements for a mobile-based embodiment of the present invention.

FIG. 8 provides a more detailed use case diagram for the invention. The use case diagram illustrates the major functions and sub functions of the invention. The first function with which the user interacts is the map view. From the map view, the user may interact with one of the other functions; well search, radius search, charts, annotations, and print functions.

The well search allows a user to search for wells based on multiple filter criteria.

The radius search allows searching for wells within a specified radius of a selected well. Radius options include all wells in the specified radius, or comparison of operators and well types in the specified radius.

The charts function shows line charts, bar charts, lost revenue potential, net present value, and internal rate of return for all wells currently displayed on the map. Line charts depict the production depletion for 12 months after the fracture date, comparing wells by specific chemical designation. Bar charts depict monthly production differences comparing wells by specific chemical designation. Lost revenue potential is calculated to illustrate the revenue lost by not using the specific chemical designation. Net present value and internal rate of return are calculated for horizontal and vertical wells with and without the specific chemical designation, to show the value of using the specific chemical designation.

The annotations function allows the user to select a single annotation, which represents a single well, and subsequently view chemical detail information and production detail information. Hazard information is available for individual chemical detail records.

The print map function will print the current map on the screen, with annotations to any printer connected via Bluetooth to the user's mobile device.

For example, a user may tap the well search function and search for wells in the state of Texas. This will return annotations on the map depicting each well returned in the search. The user may then select a single well, or annotation, and view detail chemical and production for that well. The user may also select the radius function to see all wells within a specified radius of the selected well. The user may also tap the charts function to see comparisons of production and revenue for all wells in the area compared by a specific chemical designation.

Figure 9:
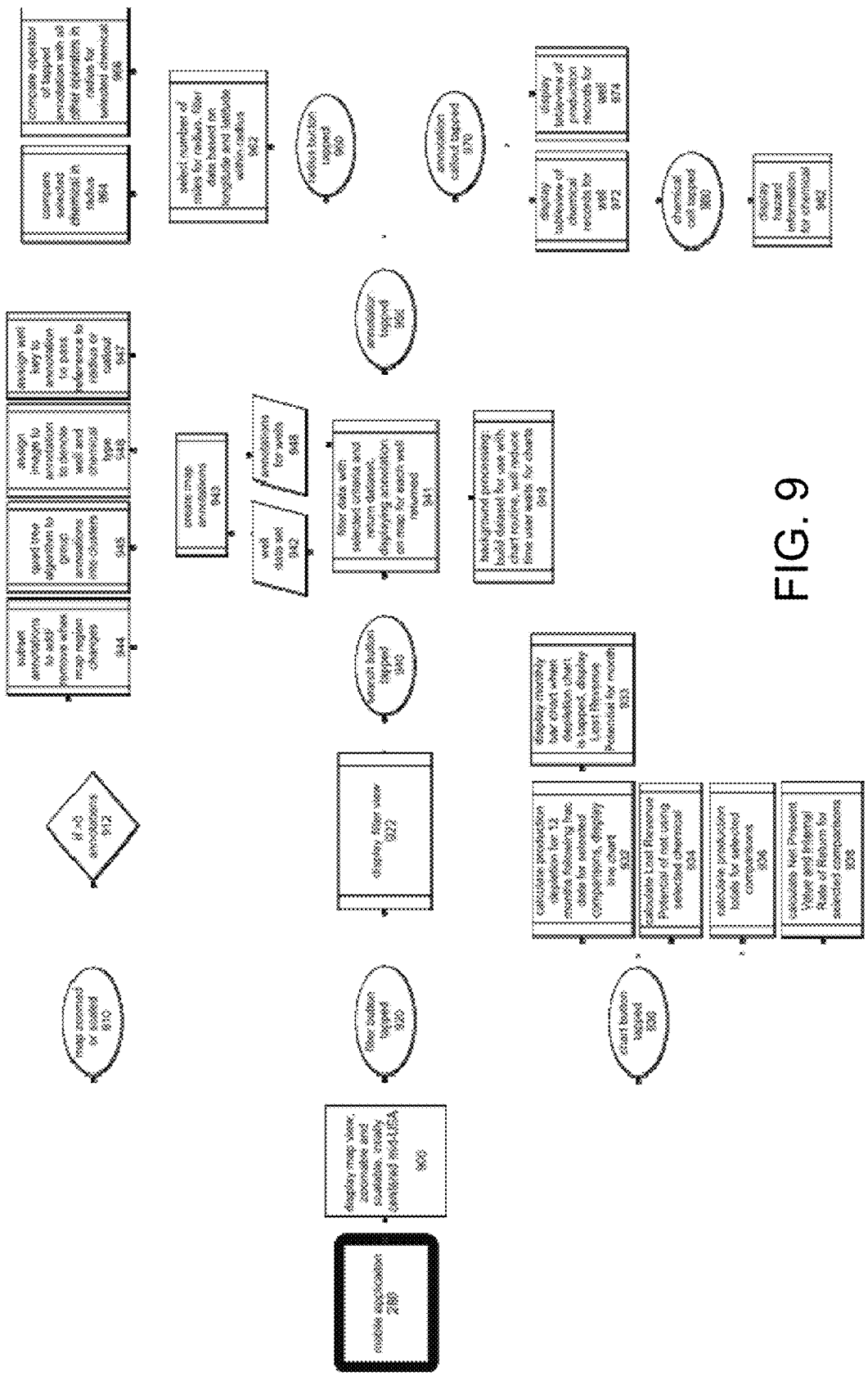
FIG. 9 is an exemplary flow diagram of the mobile application shown in FIG. 2, wherein the process steps of selecting wells and comparing data are depicted for the mobile-based embodiment of the present invention.

FIG. 9 is a detail exemplary flow diagram of a mobile-based embodiment (MBE), or mobile application, shown in FIG. 2 (Block 280), of a system for implementing the process of the present invention for oil and gas wells. In this embodiment, a user is utilizing a mobile device to access the system. The first screen presented to the user is a map view of the United States. The user may select the filter function to search for specific oil and gas wells, the chart function or zoom/scale the map. The first logical step is to select the filter function.

Selecting the filter function will generate a pop-up screen with options for selection criteria for search. The user will then tap the search button to initiate the search. For example, the user can select wells in Texas, in Karnes County, and in the Eagle Ford Shale. Upon tapping the search button, the map view will reappear with annotations for all wells in the Eagle Ford Shale in Karnes County, Tex. Annotations denote whether the well is oil or gas, and whether the well contains a specialized chemical designation, in this case a CnF® microemulsion. Annotations are clustered for areas that have multiple wells in such close proximity that annotations would overlap significantly. Annotations store data internally to reference detail data for the well represented. Annotations are re-clustered to add/remove clusters and annotations as the user zooms/scales the map.

After the annotations have been displayed, the user has several options, one of which is viewing detail information for the well. The user may tap an individual annotation to access the detail data for that individual well. When the user taps the annotation, a table listing the detail chemical data will appear. If the detail listing contains a record for the specialized chemical designation, that record will be noted with a different color. A table listing monthly production data is also available for the well. The user may toggle between production and chemical data on small or portrait orientations, or view both simultaneously on large or landscape orientations. Tapping on an individual chemical item will bring up a table listing of any associated hazards for the chemical item.

Another option after annotations are displayed is the chart function. The user may tap the chart button to view charts for all wells displayed on the map view. When the user taps the chart button, a pop-up appears which initially shows a depletion line chart for horizontal, oil wells comparing a specialized chemical designation, in this case a CnF® microemulsion. A pie chart is also displayed, showing the percent of horizontal wells that utilize a CnF® microemulsion and the percent that do not utilize a CnF® microemulsion. Lost Revenue Potential is also displayed, calculated by multiplying the production difference between horizontal oil wells utilizing a CnF® microemulsion and horizontal oil wells not utilizing a CnF® microemulsion times the oil spot price, times the number of horizontal wells not using a CnF® microemulsion. Depletion line charts using similar processing and logic are created for three other well directions and types; horizontal gas wells, vertical oil wells, and vertical gas wells. There are functions, accessible by buttons, for the other direction and well type options.

Another chart type available in the chart function is a totals chart. This chart is a tabular form showing the total lost revenue potential of all well types and directions. Net Present Value (NPV) is calculated for each well type and direction and is accessible by a button. Tapping this button initially shows a 10-year summary of NPV. Variables are available for modification, and the user may recalculate NPV with variables more appropriate for their situation. Internal Rate of Return (IRR) is calculated for each well type and direction and is accessible by a button. Tapping this button initially shows a 10-year summary of IRR. Variables are available for modification, and the user may recalculate IRR with variables more appropriate for their situation.

After annotations have been displayed another option available is a radius search. The user must select a single annotation to use the radius search. The user taps the radius button, and a pop-up appears with options to select the radius diameter and the type of search, show all wells, or compare by operator. If the user selects show all wells, all wells in the selected radius will appear. For example, the user selects a 10-mile radius and the software shows all wells and lets the user tap the "Search" button. The map view will reappear with annotations for all wells within a 10-mile radius of the selected well. The user may now view charts for that area, view detail for the selected well, or select radius again to initiate a new radius search. If the user selects compare by operator, all wells for other operators with the opposite value of the selected well's chemical designation will appear. For example, the user selects well Alpha, which has on operator of Company A and has a chemical designation of no CnF® microemulsion use, the map view will reappear with all of Company A's wells and all wells from all other operators with a chemical designation indicating a use of a CnF® microemulsion.

Referring now to FIGS. 10-22, the MBE is depicted through a series of screen shots from a mobile application provided by the inventors. Those skilled in the art appreciate; however, that embodiments of the present invention and the inventors embodiment may vary substantially or insubstantially in the features and functions provided by such systems without departing from, modifying, adding, or deleting to the scope of the present invention as described herein and expressed in the claims.

Figure 10:
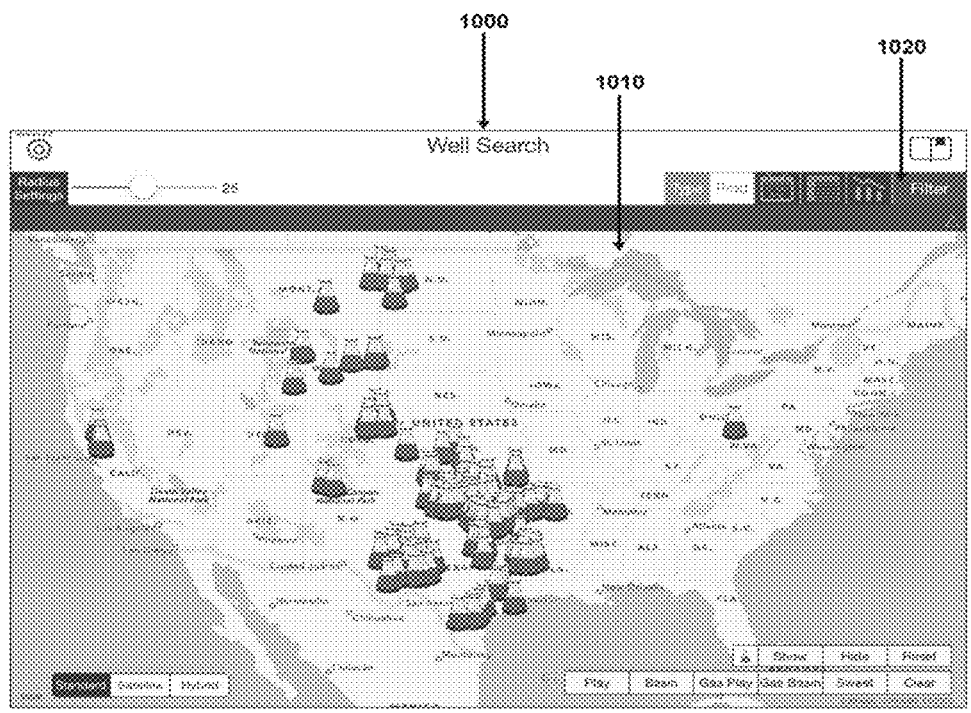
FIG. 10 is an exemplary screen shot of the initial map view for a mobile-based embodiment of the present invention.
Figure 11:
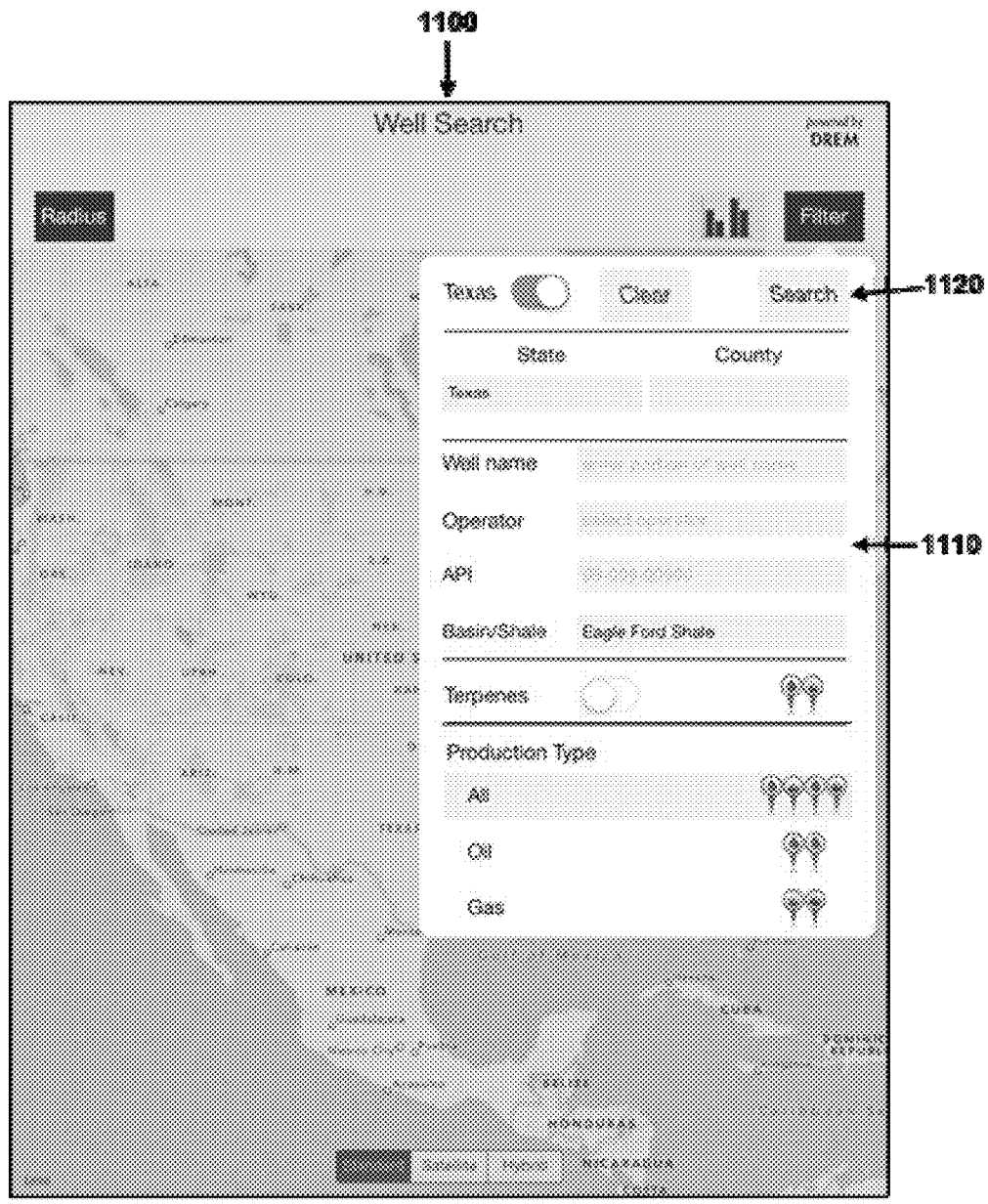
FIG. 11 is an exemplary screen shot of the search filter for a mobile-based embodiment of the present invention.

As shown in FIG. 10, the primary view of the MBE is a map view (1010). Oil and gas wells are accessed by using the Filter button (1020) to search the mobile data store. Tapping the Filter button initiates a pop-up with selection criteria options (1110), as shown in FIG. 11. As an example, in this screen shot, the state of Texas, and the Eagle Ford Shale are selected. Tapping the Search button (1120) removes the pop-up and the map view appears with annotations for each well, as shown in FIG. 12.

Figure 12:
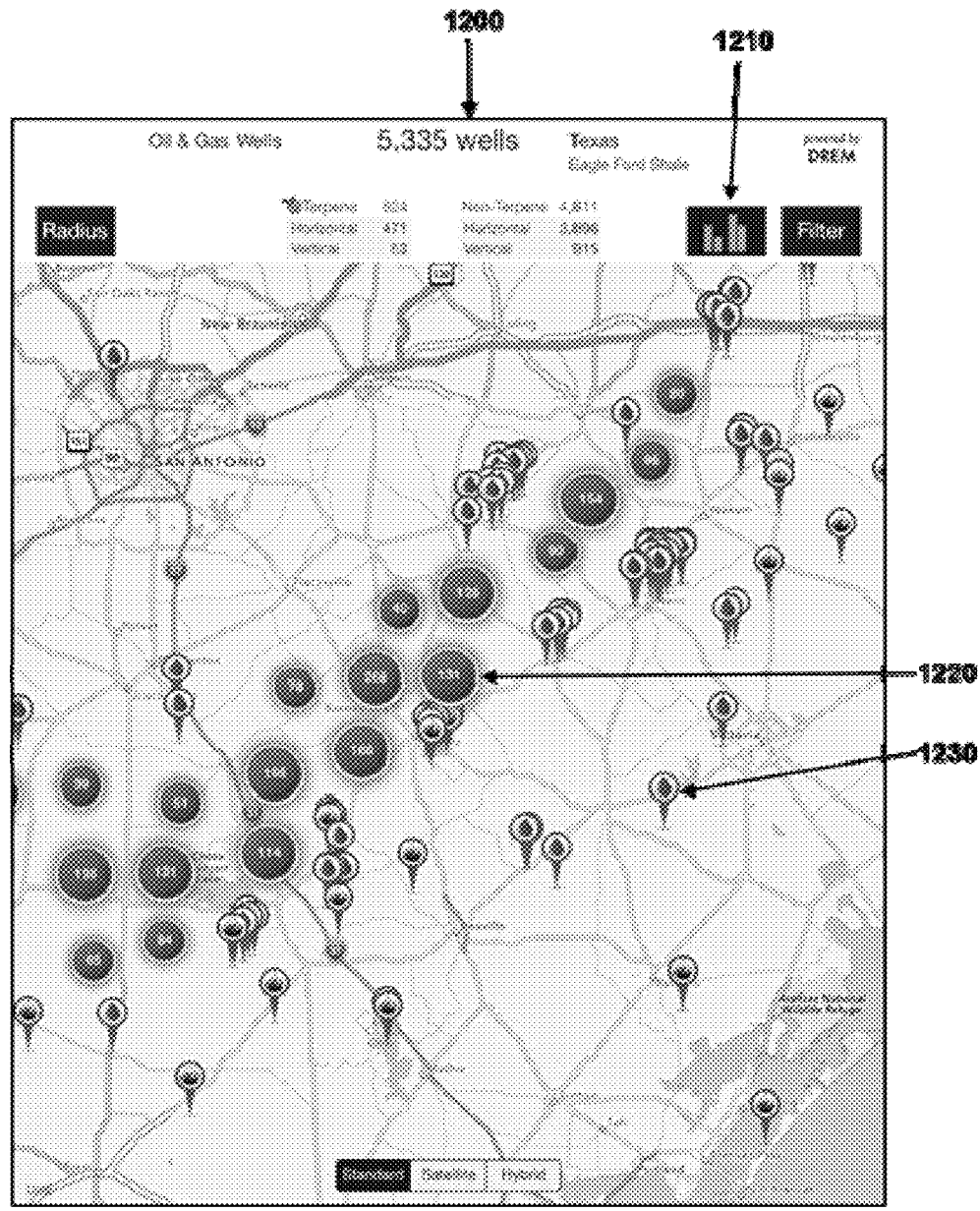
FIG. 12 is an exemplary screen shot of the search results and annotations, representing oil and gas wells, for a mobile-based embodiment of the present invention.
Figure 13:
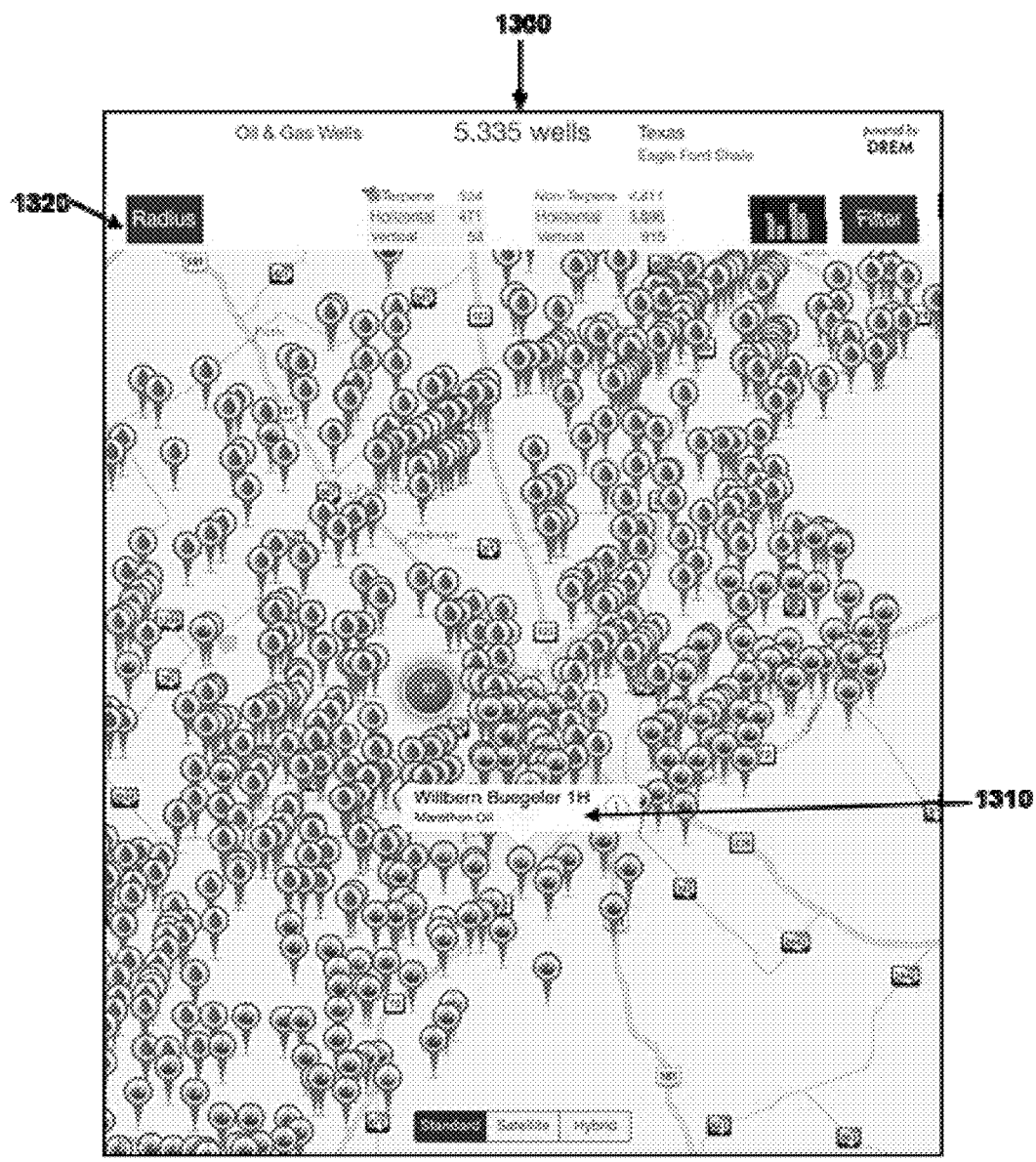
FIG. 13 is an exemplary screen shot of the selection of an individual well for a mobile-based embodiment of the present invention.

Also shown in FIG. 12, annotations are clustered (1220), with the number of wells in each cluster noted, for areas where there are too many wells to show without significant overlapping of annotations. Annotations with ample space to show individual wells are displayed with an image denoting the well type (1230). Annotations de-cluster as the map is zoomed out, as shown in FIG. 13.

Figure 14:
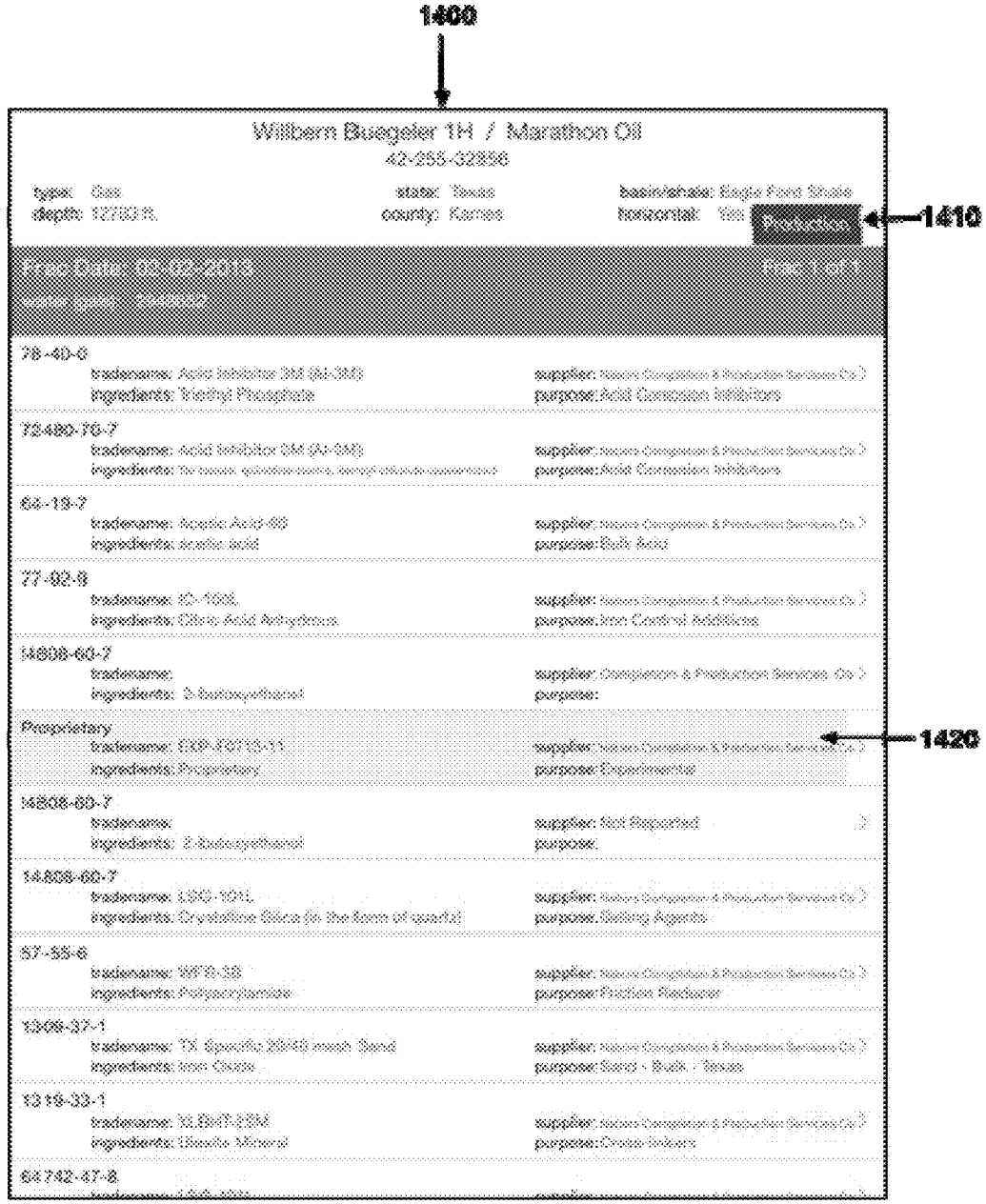
FIG. 14 is an exemplary screen shot of the chemical detail view for an individual well for a mobile-based embodiment of the present invention.
Figure 15:
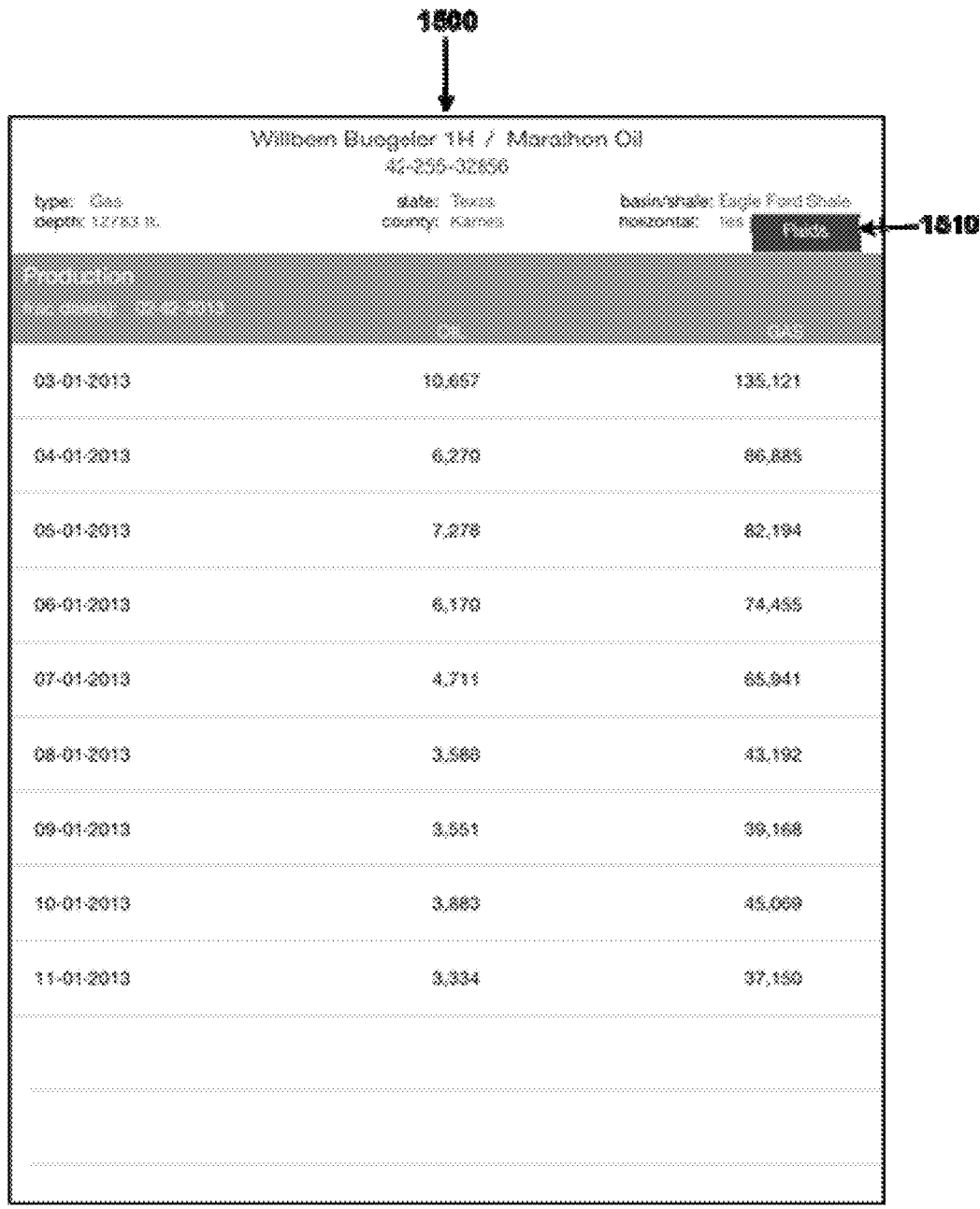
FIG. 15 is an exemplary screen shot of the monthly production average detail listing for a single well for a mobile-based embodiment of the present invention.

Selection of an individual well will display a view above the well (1310) with additional information. Tapping on the view above the well will initiate the display of a table listing of detail chemical records for the well, as shown in FIG. 14. If the well contains a specialized chemical designation, it will appear in a different color. For example, the chemical record colored light gray (1420) is a specialized chemical designation. There is a Production button (1410) which, when tapped, will display the monthly production for the well as shown in FIG. 15.

Figure 16:
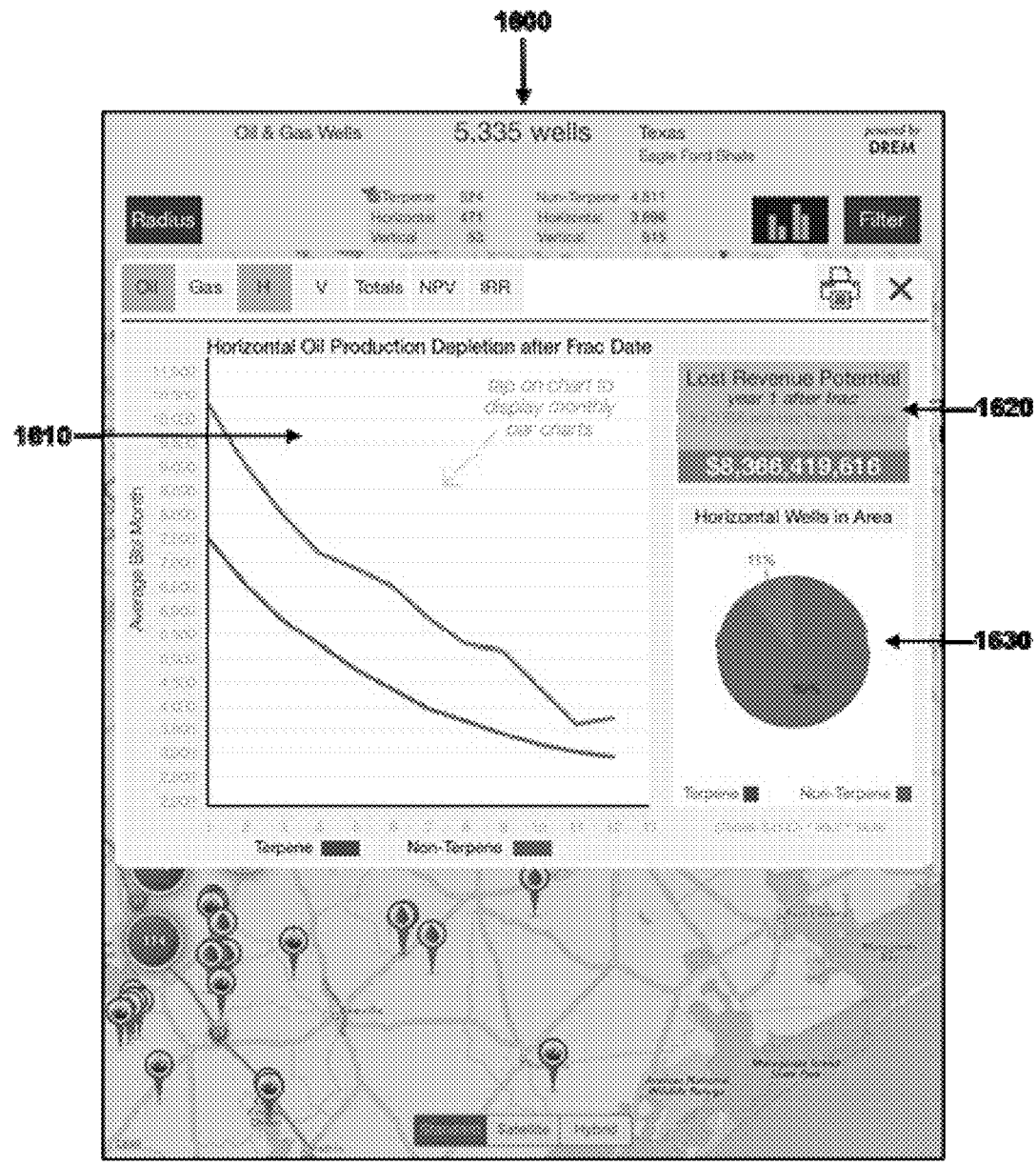
FIG. 16 is an exemplary screen shot of the chart function showing production depletion comparison for wells in an area compared by chemical designation for a mobile-based embodiment of the present invention.
Figure 17:
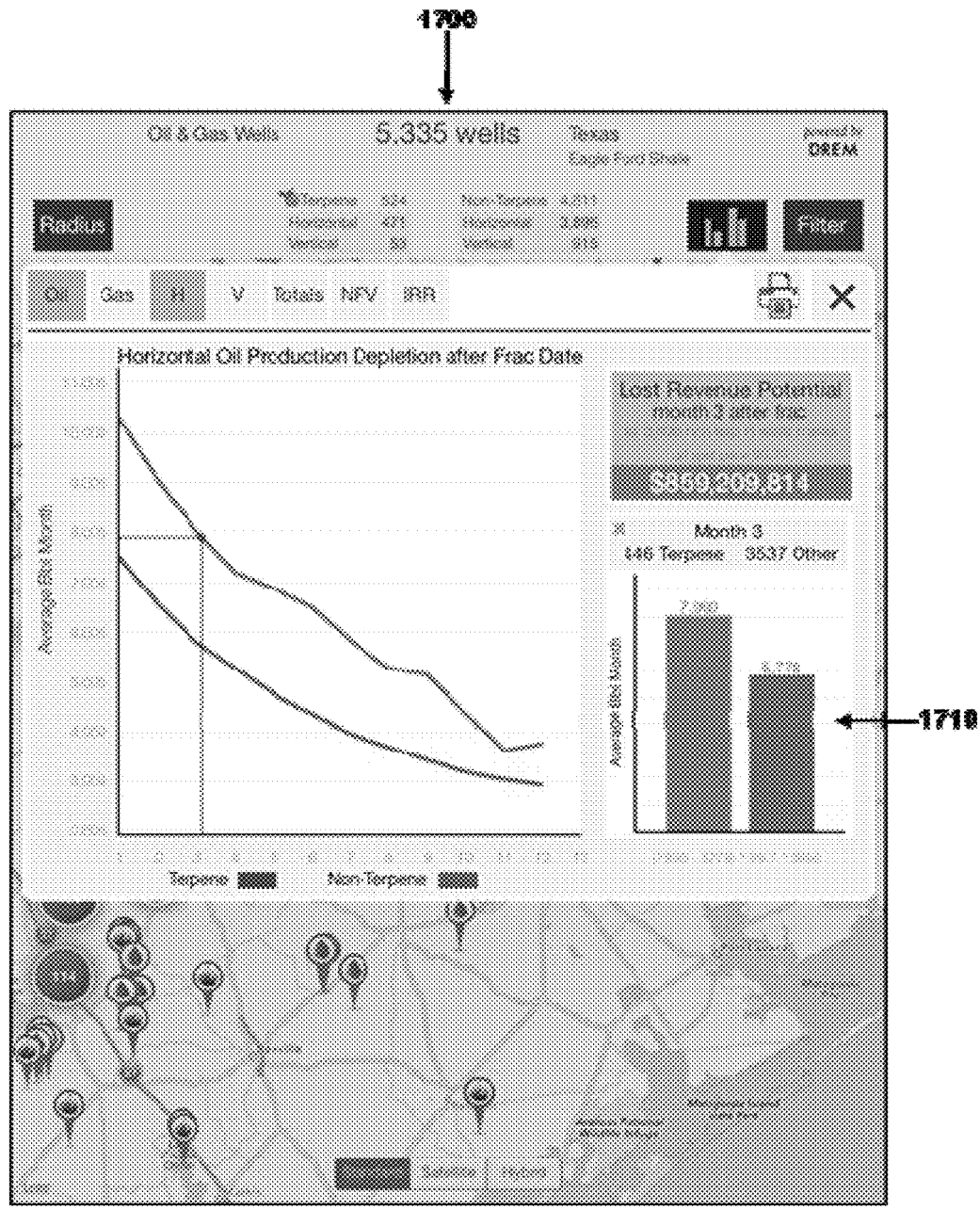
FIG. 17 is an exemplary screen shot of the monthly bar chart showing a single month's production for wells in an area compared by chemical designation for a mobile-based embodiment of the present invention.
Figure 18:
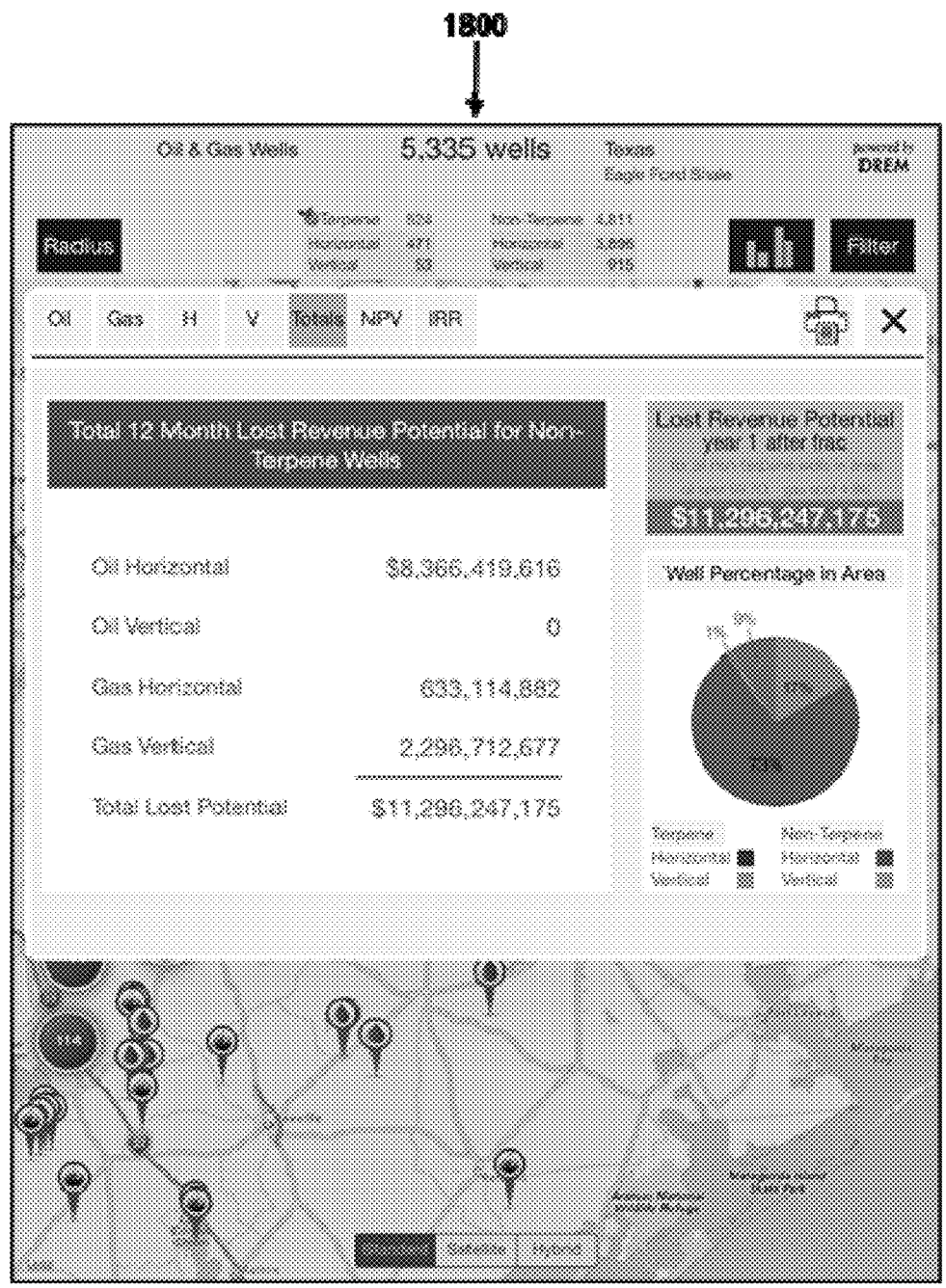
FIG. 18 is an exemplary screen shot of the total lost revenue potential for wells in an area compared by chemical designation for a mobile-based embodiment of the present invention.
Figure 19:
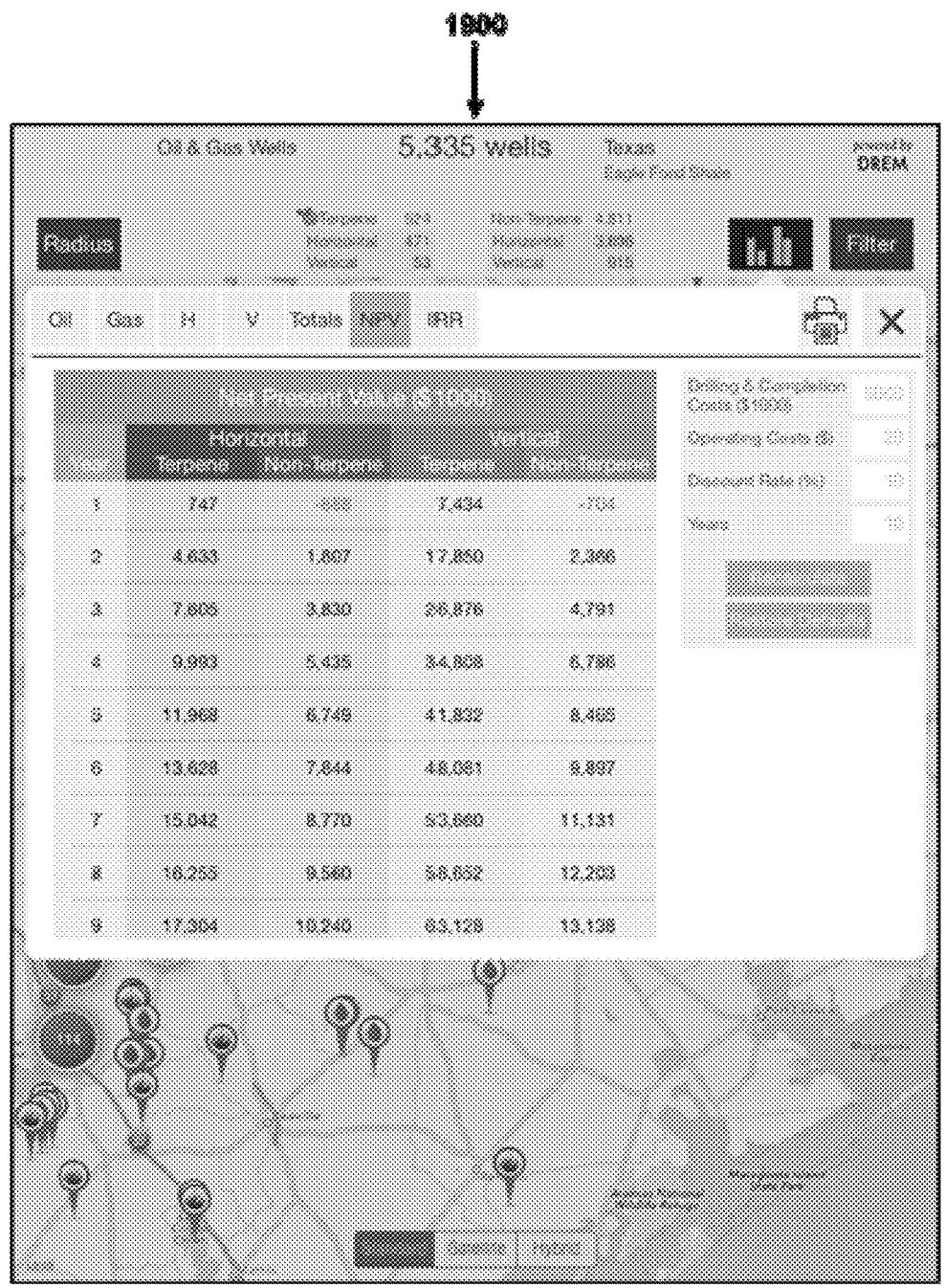
FIG. 19 is an exemplary screen shot of the net present value for wells in an area compared by chemical designation for a mobile-based embodiment of the present invention.
Figure 20:
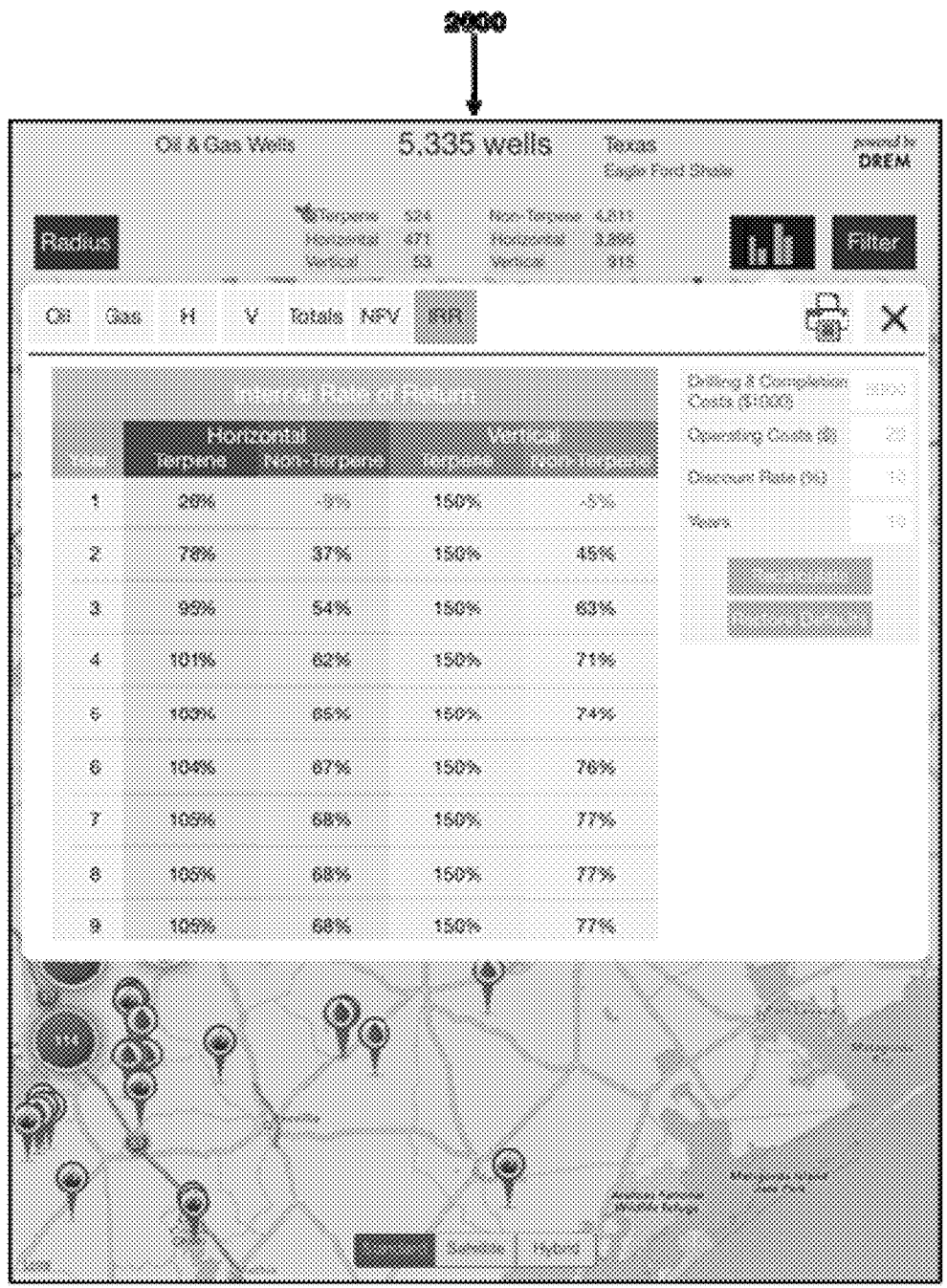
FIG. 20 is an exemplary screen shot of the internal rate of return for wells in an area compared by chemical designation for a mobile-based embodiment of the present invention.

Referring back to FIG. 12, showing the annotations after a search, the user may choose to view charts at this point by tapping the chart button (1220). After tapping the chart button, a pop-up appears showing a depletion line chart (1610) comparing wells with CnF® microemulsion use and wells without CnF® microemulsion use, lost potential revenue (1620) of not using a CnF® microemulsion, and a pie chart (1630) for horizontal oil wells utilizing a CnF® microemulsion and not utilizing a CnF® microemulsion in the state of Texas, and the Eagle Ford Shale, as shown in FIG. 16. Tapping on the depletion line chart (1610) displays a monthly bar chart (1710) comparing production of wells using CnF® microemulsions and non-CnF® microemulsion using wells, as shown in FIG. 17. Additional charts available, which compare wells utilizing CnF® microemulsions with wells not utilizing CnF® microemulsions, are illustrated in FIGS. 18-20, including showing Totals, Net Present Value, and Internal Rate of Return.

Figure 21:
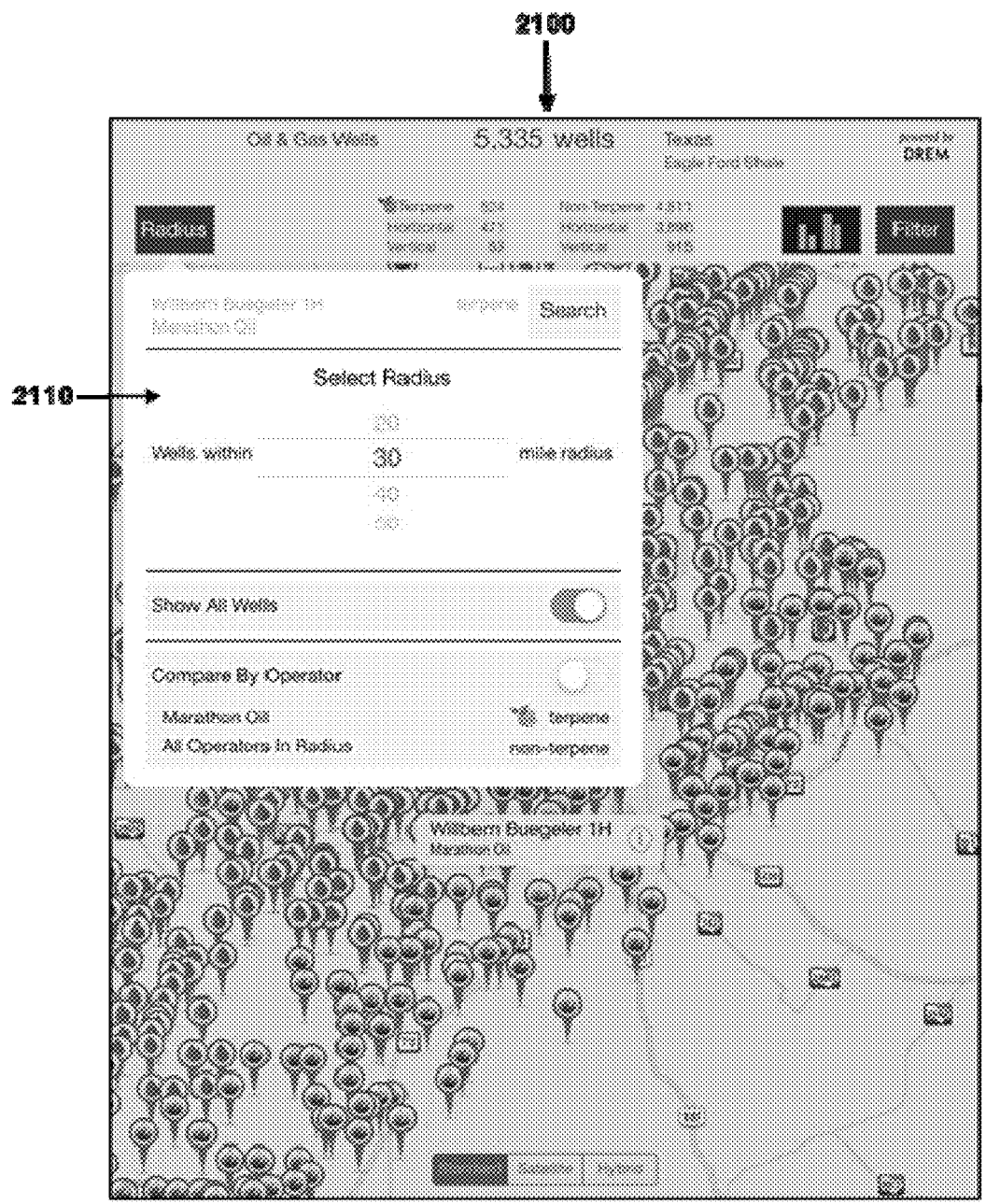
FIG. 21 is an exemplary screen shot of the radius search function for a mobile-based embodiment of the present invention.
Figure 22:
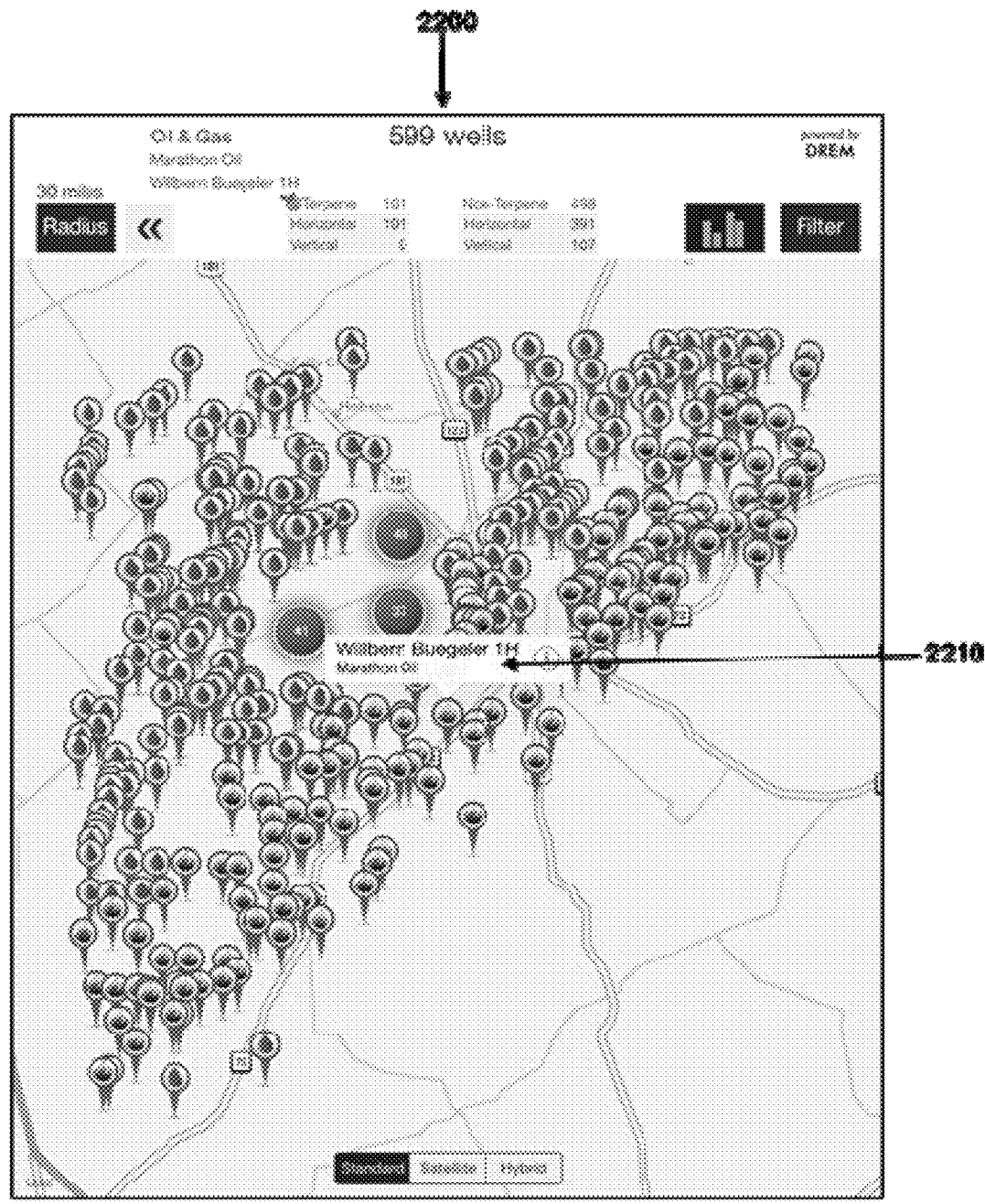
FIG. 22 is an exemplary screen shot of the search results for the radius search function for a mobile-based embodiment of the present invention.

Referring back to FIG. 13, the user has selected an individual annotation, or single well. The user may now use the Radius button (1320) to get wells within a radius of the selected well. When the user taps the Radius button, a pop-up appears, as shown in FIG. 21, with a selection for the radius in miles, and options to show all wells in the radius, or compare operators in the radius. In this example, the user has selected to show all wells in a 30-mile radius (2110). The result is shown in FIG. 22. The map view reappears with the annotations for all wells in a 30-mile radius of the well selected. The well selected (2210) appears in the middle of the radius. At this point, the user may continue the process stated above and view charts, view detail for the selected well, initiate another filter search, or initiate another radius search.

User Interface Detailed Examples

Figure 23:
FIG. 23 is an exemplary screen shot of estimated recovery period, in months, for the cost of utilizing the specific, specialized chemical for fracturing a well.

FIG. 23 is an exemplary screen shot of the estimated recovery period, in months, for the cost of utilizing the specific, specialized chemical for fracturing a well. The cost of the chemical is recovered when a checkmark appears in the "CnF® Cost Recovered" column. Variables can be edited to customize the cost recovery model.

Figure 24:
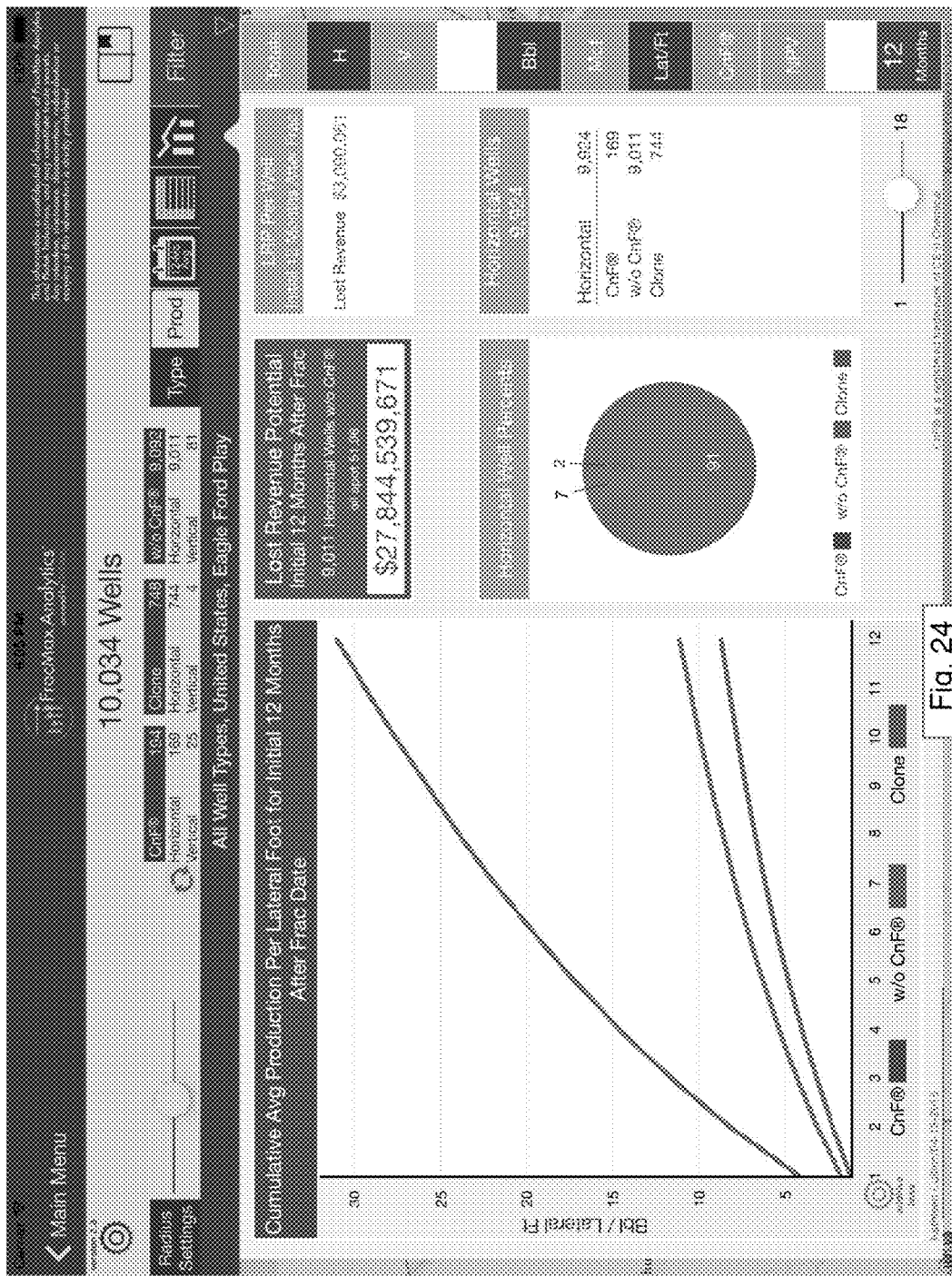
FIG. 24 is an exemplary screen shot of the cumulative production average per lateral foot for horizontal wells in the search area.

FIG. 24 is an exemplary screen shot of the cumulative production average per lateral foot for horizontal wells in the search area. Averages are compared for wells utilizing the specific, specialized chemical, wells utilizing other specialized chemicals, and all other wells. The initial line chart show 12 months of production. The number of months for charting and comparison can be changed using the slider on the bottom right of the screen shot.

Figure 25:
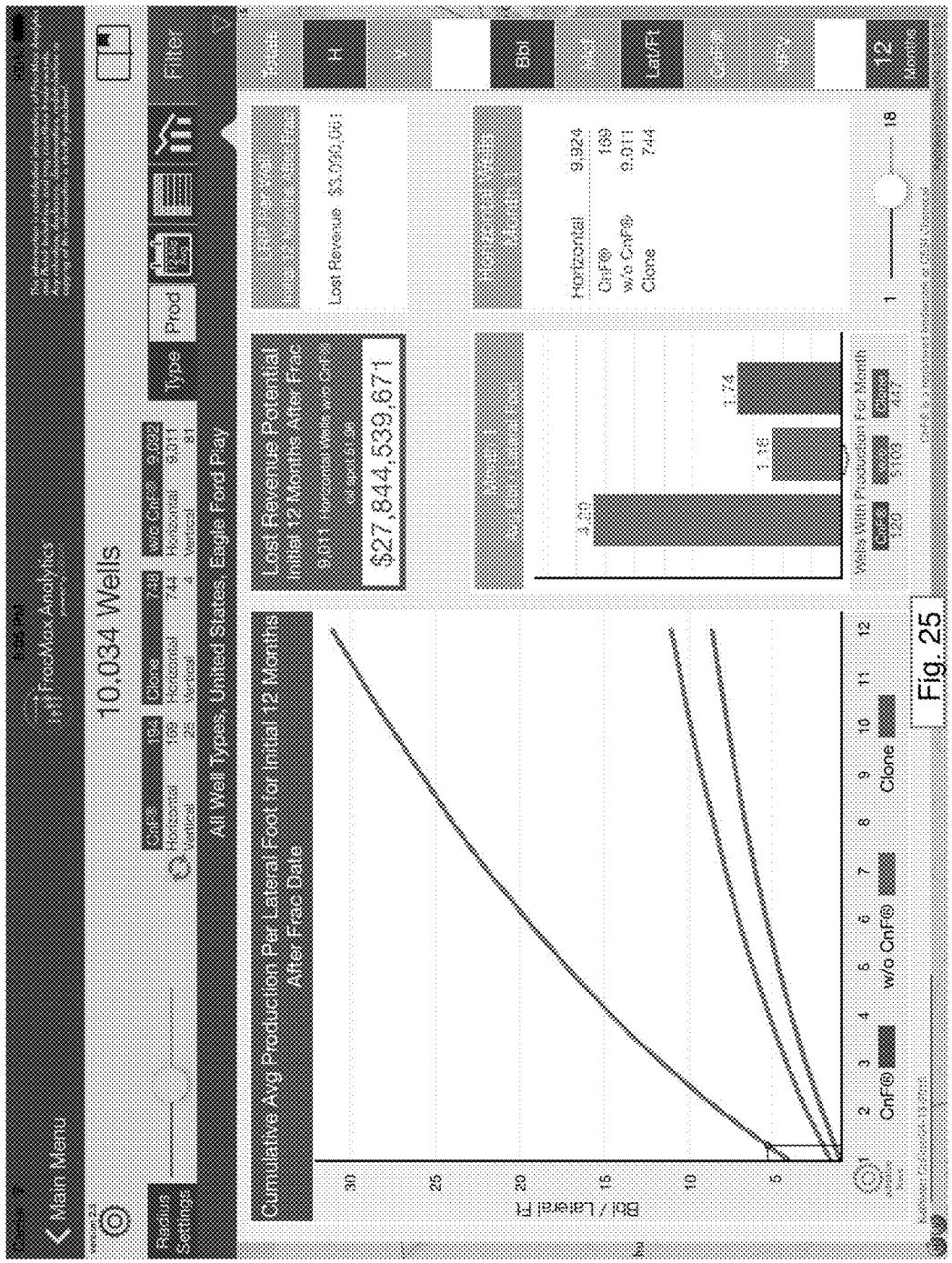
FIG. 25 is an exemplary screen shot of the monthly bar chart for production average per lateral foot.

FIG. 25 is an exemplary screen shot of the monthly bar chart for production average per lateral foot. This screen appears when a swipe motion is initiated on the cumulative average production line chart. The bar chart changes to reflect production for the month that is being touched on the line chart.

Figure 26:
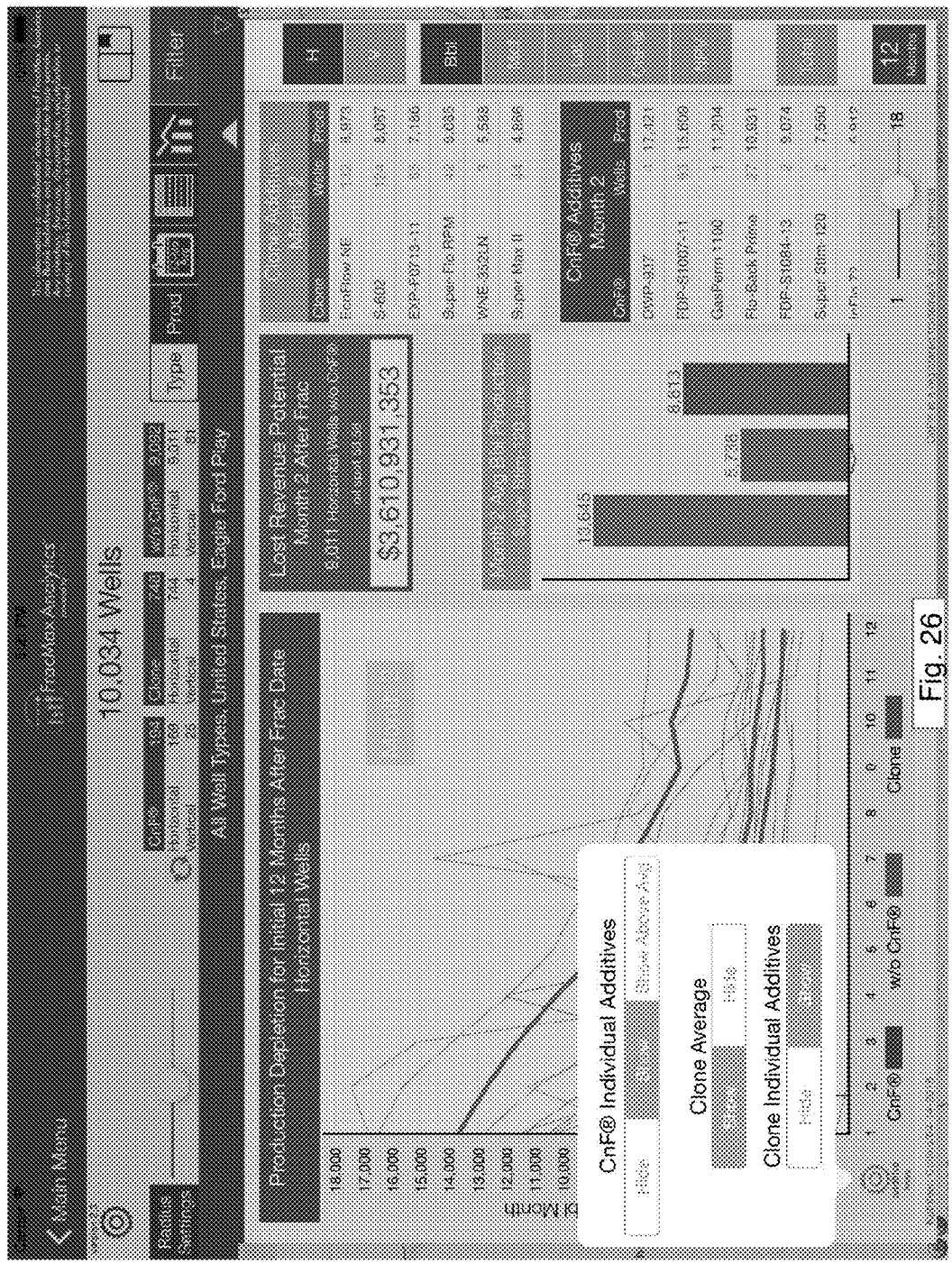
FIG. 26 is an exemplary screen shot of the chart line options for depletion charts.

FIG. 26 is an exemplary screen shot of the chart line options for depletion charts. Options include the ability to view lines for individual specialized chemicals, the ability to hide the line for other specialized chemicals, and view individual lines for the other specialized chemicals. The individual specialized chemical lines will appear in different colors and thinner lines. Upon swiping on the depletion charts, monthly bar charts will appear. Tables will also appear on the right side of the screen listing each individual chemical, with well counts and average production reflecting the month currently being touched on the depletion chart.

Figure 27:
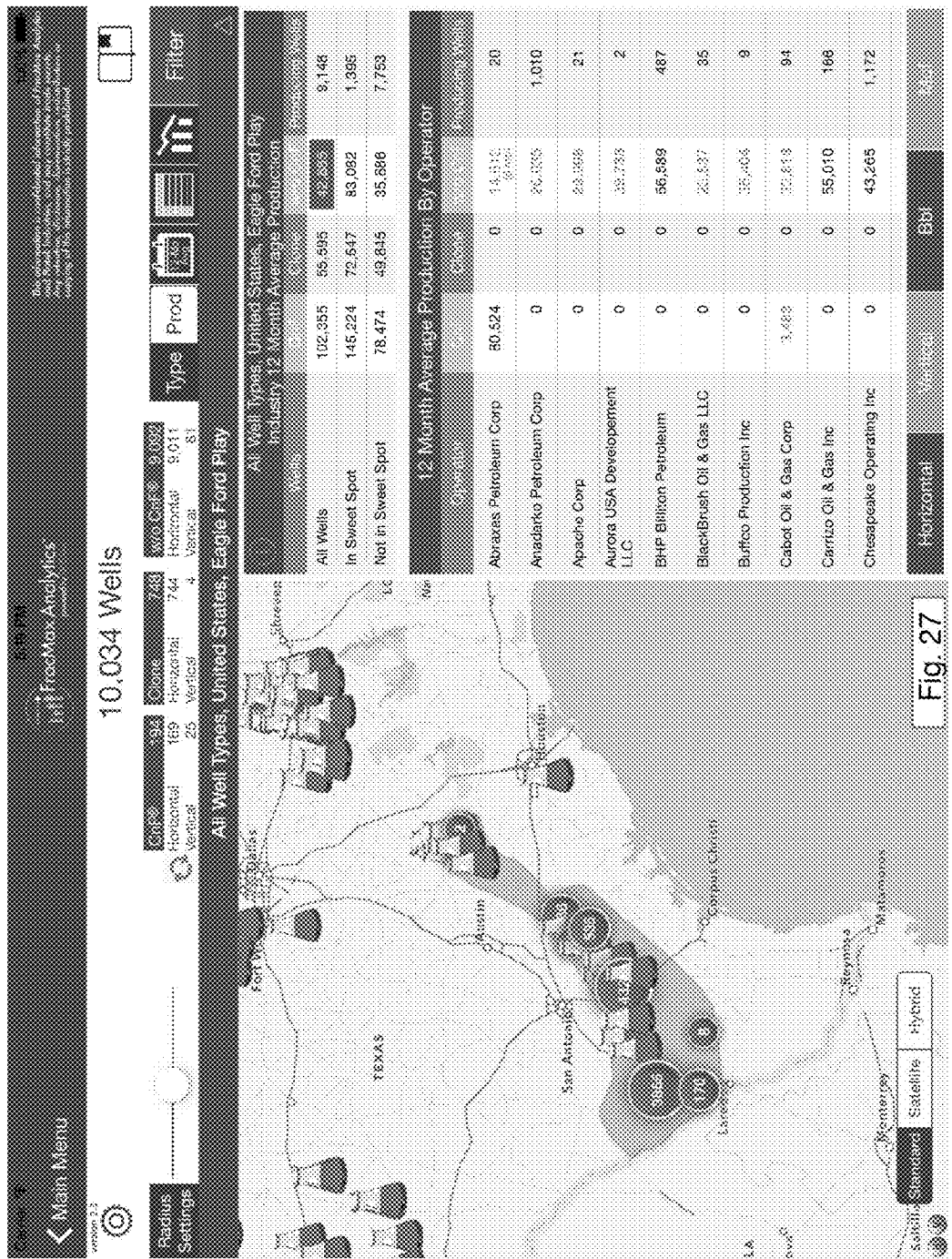
FIG. 27 is an exemplary screen shot of a "12-Month Average" feature.

FIG. 27 is an exemplary screen shot of a 12 month averaging feature, accessed by tapping on the 12-Month icon, the fourth icon from the right on the screen shot. The 12-Month feature displays two tables for the wells in the area. The top-most table shows production averages for 12 months. Production is broken down by "In Sweet Spot" and "Not in Sweet Spot". "In Sweet Spot" refers to wells that are in the area designated as the area with optimum production for the geological formation in the search area. "Not in Sweet Spot" are wells that are not in the area with optimum production. The highlighted "w/o CnF" number is considered the production benchmark for the area. The bottommost table is a scrolling table view, which shows 12-month production averages by operator within the area. Production averages that are below the benchmark are marked in red in the full color embodiment of the application. Production averages that are below the benchmark, but have less than 12 months of production are marked in orange with the number of months displayed.

Figure 28:
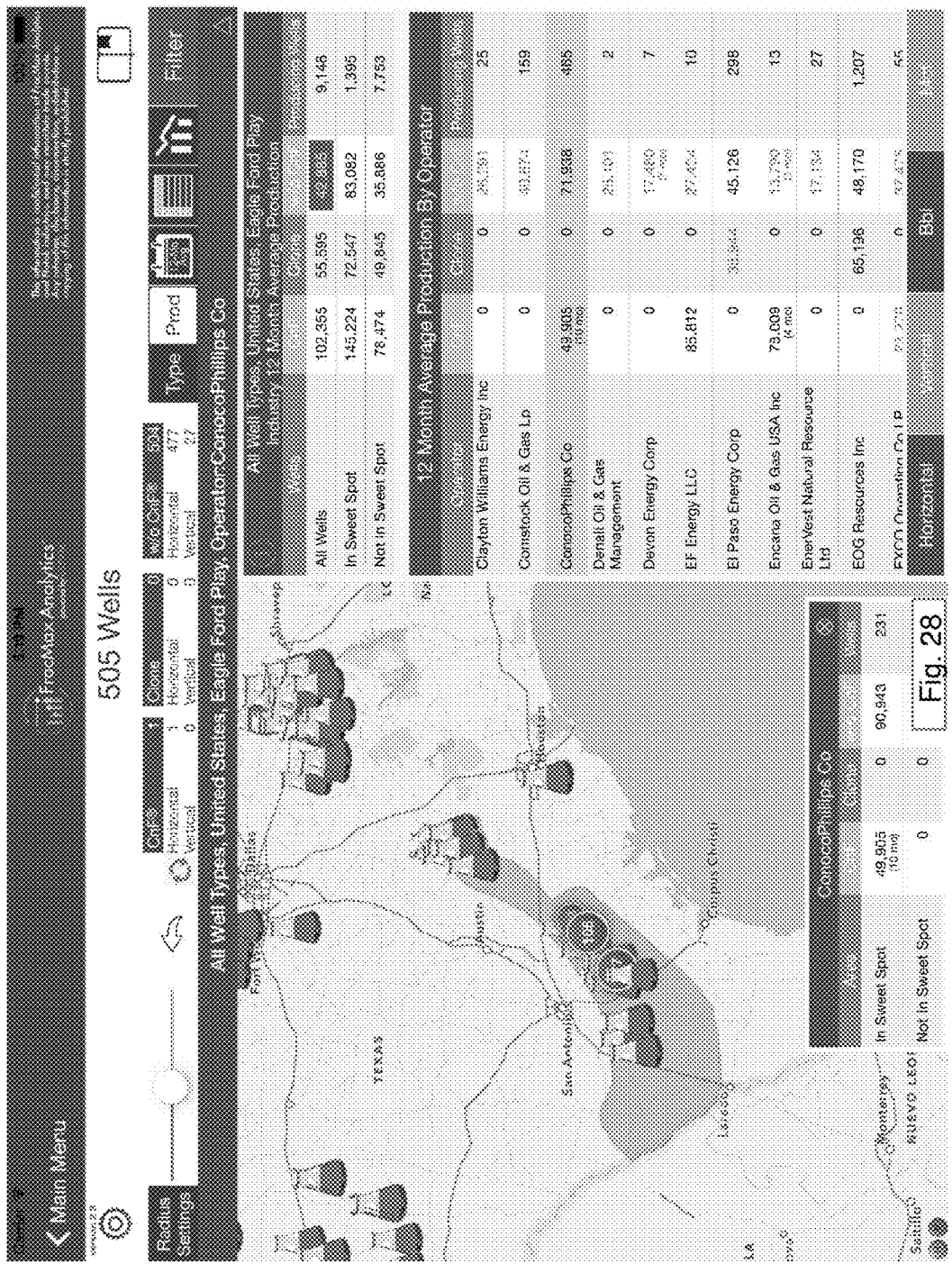
FIG. 28 is an exemplary screen shot of the display following that of FIG. 27.

FIG. 28 is an exemplary screen shot of the display when an individual operator row was tapped on FIG. 27. The map display changes to show only wells for the specified operator. Another table appears which shows the operator averages broken down by "In Sweet Spot" and "Not in Sweet Spot".

Figure 29:
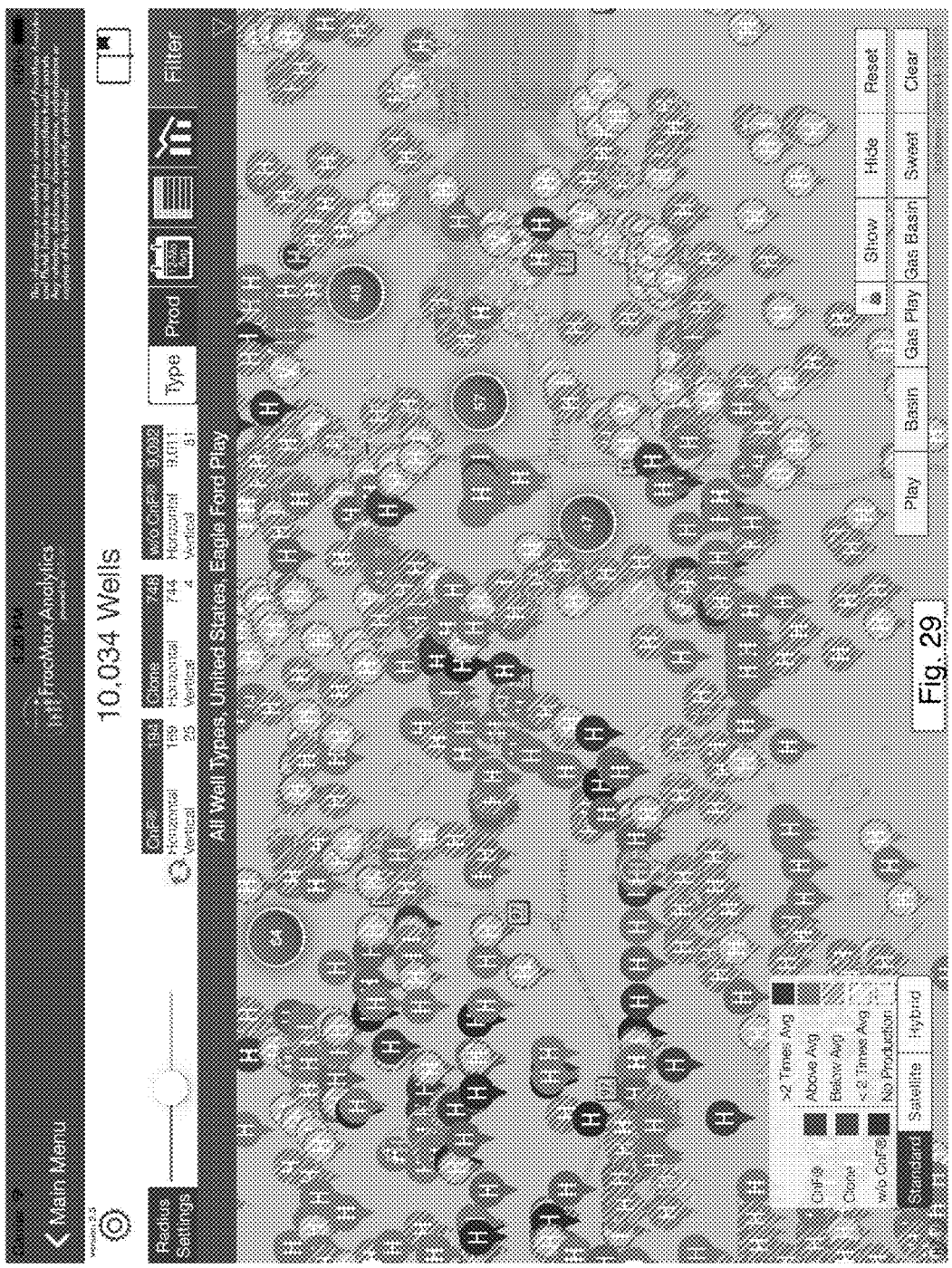
FIG. 29 is an exemplary screen shot of the production map pins.

FIG. 29 is an exemplary screen shot of the production map pins. Production map pins indicate the production value of each well in the area compared to other wells in the area. Production pins also indicate well direction, with an H or a V, and chemical designation by pin color.

Figure 30:
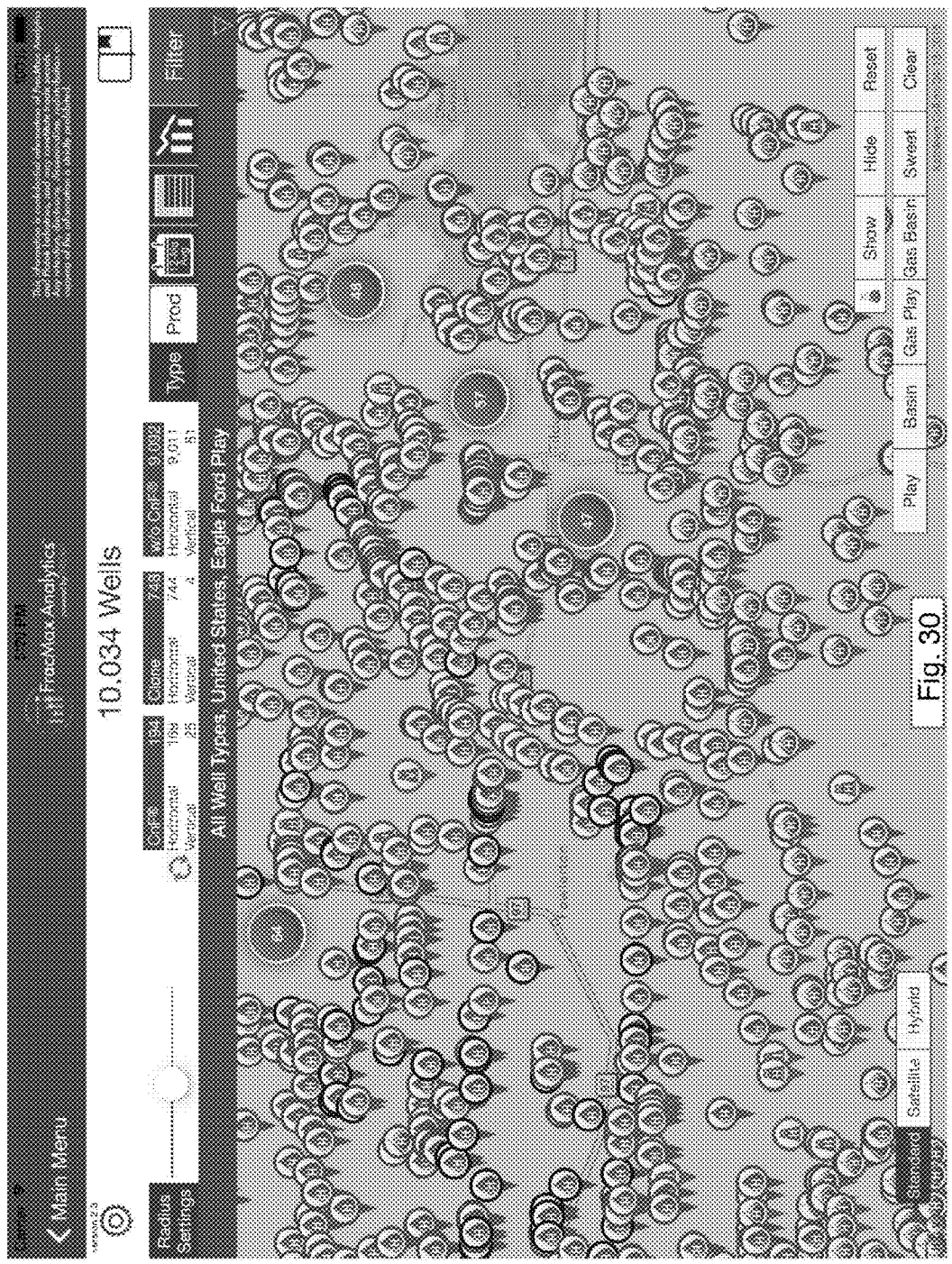
FIG. 30 is an exemplary screen shot of the well type map pins.

FIG. 30 is an exemplary screen shot of the well type map pins. Well type pins indicate well direction with an H or a V, production type by color and graphic, and chemical designation with a circular color band around the pin.

Figure 31:
FIG. 31 is an exemplary screen shot of a table showing chemicals for wells.

FIG. 31 is an exemplary screen shot of a table showing specific, specialized chemicals for wells in the search area. This table is access by tapping on the "tables" icon, the third icon from the right on the screen shot. Counts are sortable by Operator and Service Company.

Figure 32:
FIG. 32 is an exemplary screen shot of a table showing wells grouped by features.

FIG. 32 is an exemplary screen shot of a table showing wells with a specific, specialized chemical for wells in the search area grouped by operator, accessed via the "tables" icon. Wells can also be grouped by fracture date, additive (chemical), or Service Company. Groupings can be sorted alphabetically, or by well count.

Figure 33:
FIG. 33 is an exemplary screen shot of a table showing wells grouped by features.

FIG. 33 is an exemplary screen shot of a table showing wells with other specialized chemicals for wells in the search area grouped by operator, accessed via the "tables" icon. Wells can also be grouped by fracture date, additive (chemical), or Service Company. Groupings can be sorted alphabetically, or by well count.

FIG. 34 is an exemplary screen shot of a table showing wells without specified specialized chemicals for wells in the search area grouped by operator, accessed via the "tables" icon. Wells can also be grouped by fracture date, additive (chemical), or Service Company. Groupings can be sorted alphabetically, or by well count.

Figure 35:
FIG. 35 is an exemplary screen shot of a display following that of FIG. 34.

FIG. 35 is an exemplary screen shot of a table showing individual wells when a specific operator row was tapped on FIG. 34. Wells can be sorted in multiple ways.

Figure 36:
FIG. 36 is an exemplary screen shot showing chemical and production detail.

FIG. 36 is an exemplary screen shot showing chemical and production detail for an individual well when an individual well was tapped on FIG. 35.

Figure 37:
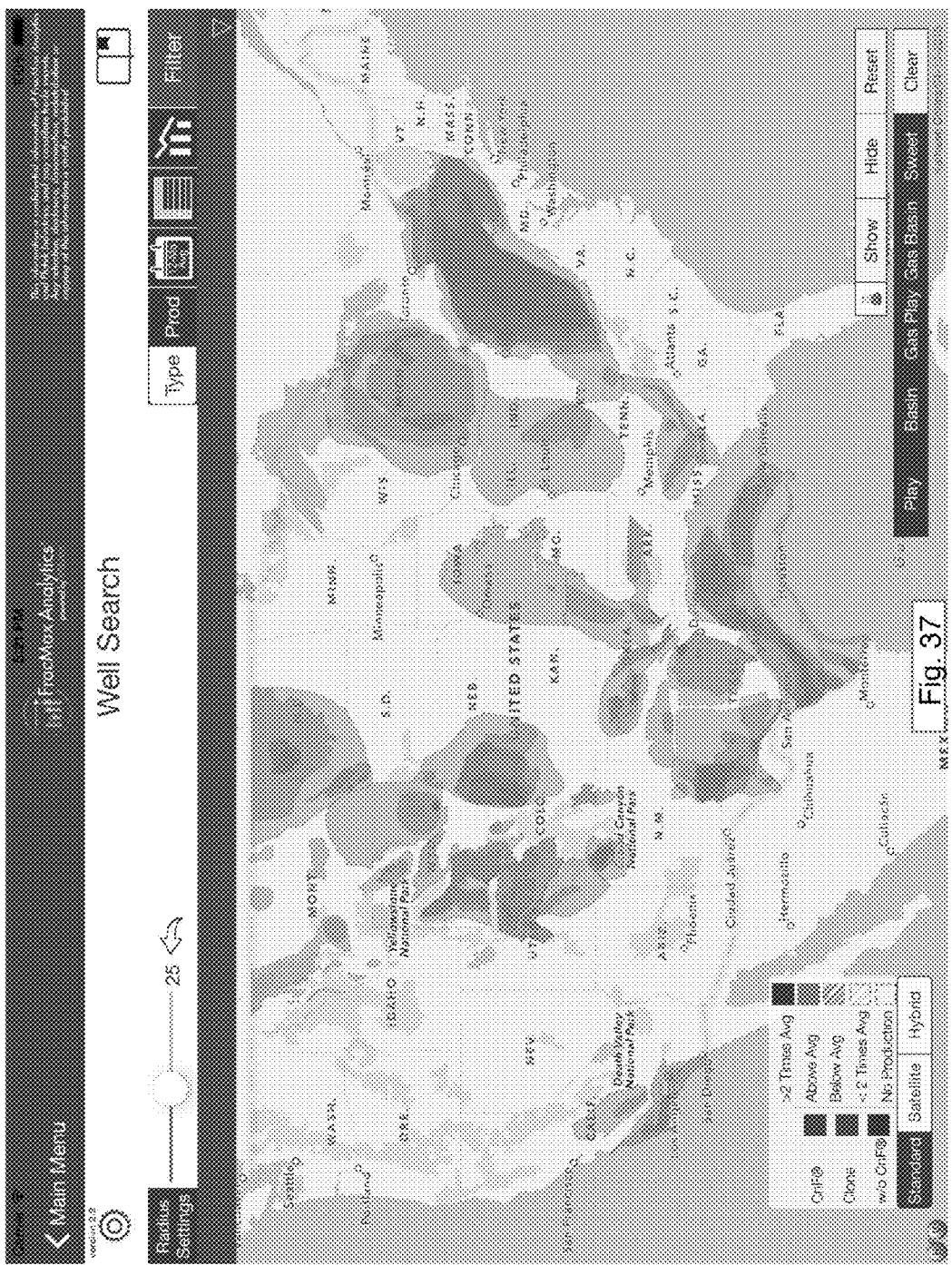
FIG. 37 is an exemplary screen shot of map overlays.

FIG. 37 is an exemplary screen shot of map overlays of basins, plays, and sweet spots in the United States which can be added to the map view by tapping on the segmented controller on the bottom right of the screen shot. Overlays can be added and removed by type.

Figure 38:
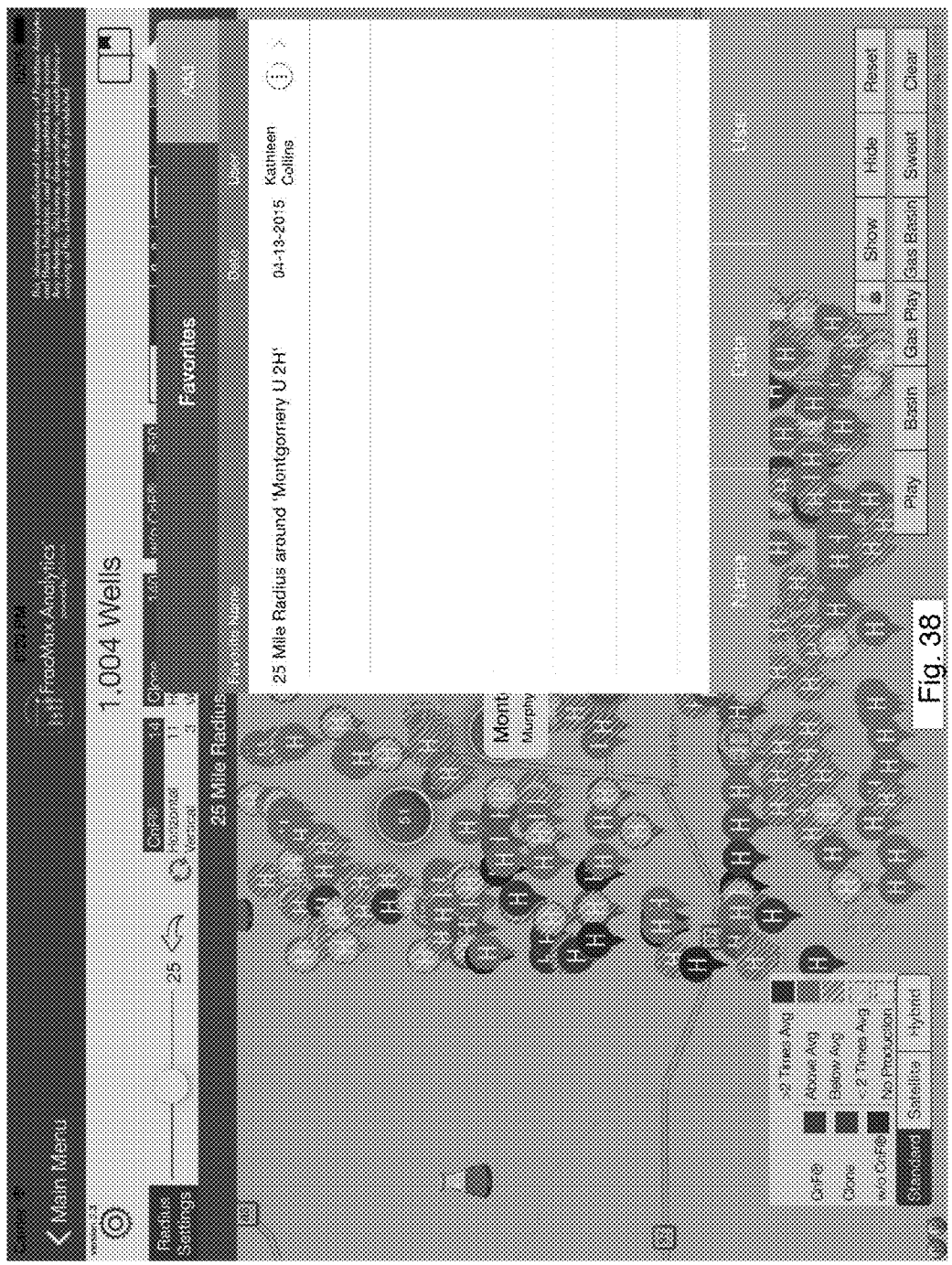
FIG. 38 is an exemplary screen shot of a favorites feature.

FIG. 38 is an exemplary screen shot of the favorites feature. Search filters can be added and saved as a "favorite". Favorites can be used to initiate searches. Favorites can also be mailed to other users of the application. When a favorite is opened in the mail application on an iPad, the favorite can be opened in the mobile application and added to the favorites. Favorites can be sorted by name, date, and originating user.

Insurance Underwriting

Use of the data above may also be used for insurance and risk management or oil and gas exploration. In particular, the analysis may be used or the underwriting of efficacy insurance. For example, if there is hesitation or reluctance on the part of the buyer to purchase the product, the seller may guarantee or warrant the efficacy of the product to the extent, for example, the cost of the product in the drilling process. An insurance product may be underwritten to stand behind that guarantee or warranty of the product by the seller based on the same comparison of data at whatever level of granularity or representative comparison of existing well data to substantiate taking the risk, even in the establishment of the premium and self-insured retentions. By way of example, the NPV and IRR examples given above may change or be augmented to include underwriting guidelines such as premium pricing, self-insured retentions, and other commonly known insurance related parameters. In particular, this may specifically include insurance that provides balance sheet protection to the provider of warranties or guarantees as to the efficacy of a product such as CNF.

In FIGS. 39-45, a series of screen shots from an application that might be implemented are shown. Embodiments of the present invention and the embodiments described herein may vary substantially or insubstantially in the features and functions provided by such systems without departing from, modifying, adding, deleting, to the scope of the present invention as described herein and expressed in the claims. Each of these screen shots can be presented as part of a user interface of a computer program that runs to present the information shown in the screen shots at an appropriate time in the execution of the computer program.

Figure 39:
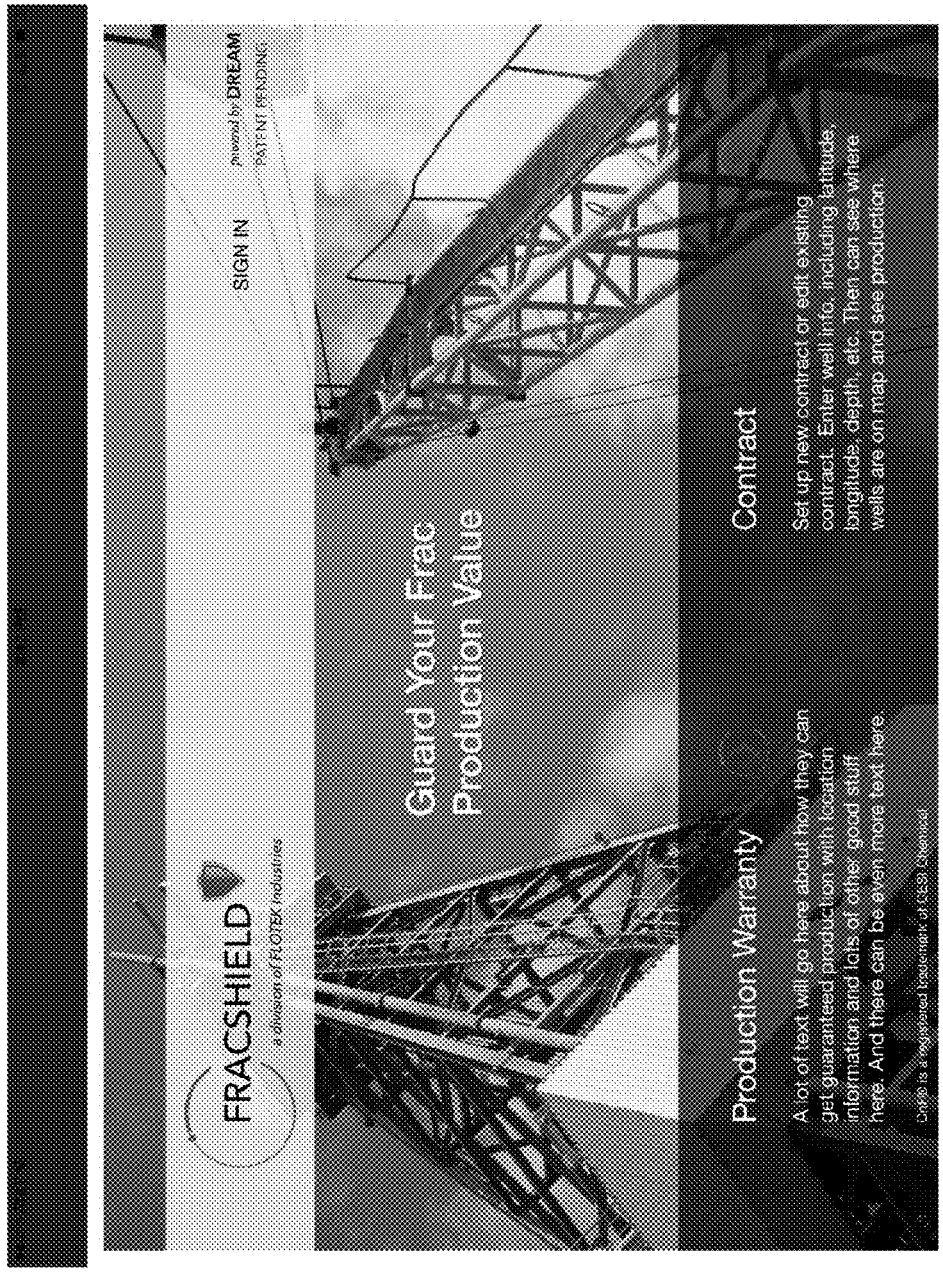

FIG. 39 is an overview template that includes the ability to access a warranty contract to warrant the efficacy of the use of a specific product in one or more products for oil and gas production. It also provides access to one or more access points to use the data assimilated and analyzed in the invention as described hereinabove to underwrite and otherwise analyze the efficacy of the product across the one or more wells. The primary options are to either (1) define, review or modify the projected wells to be warrantied against the effectiveness of the oil and gas product to be applied, or (2) analyze contract data against a series of parameters to determine the appropriate risk and pricing of an efficacy warranty and/or underlying insurance product to stand behind the efficacy warranty or product that embodies that efficacy warranty.

Figure 40:
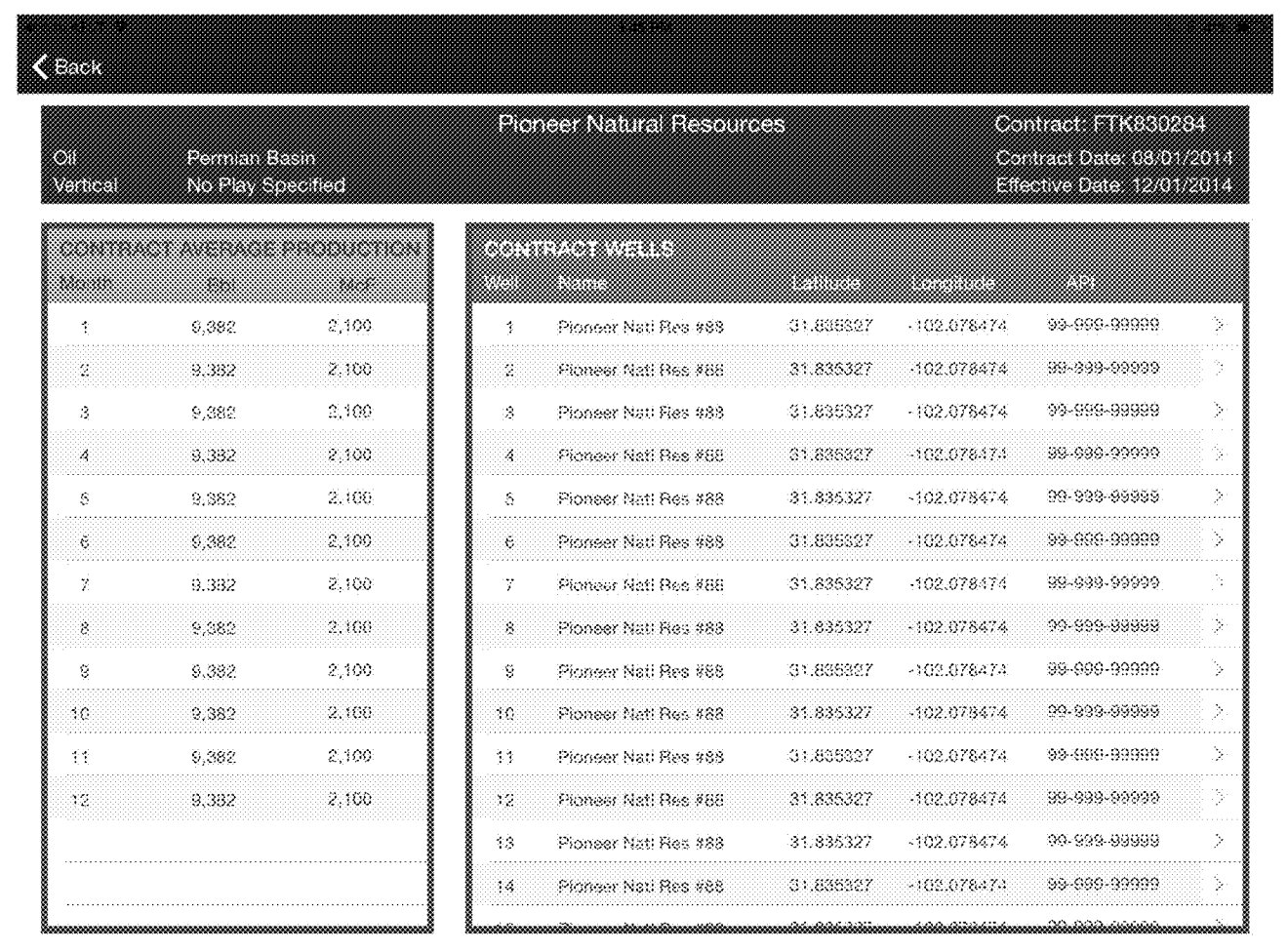
Figure 41:
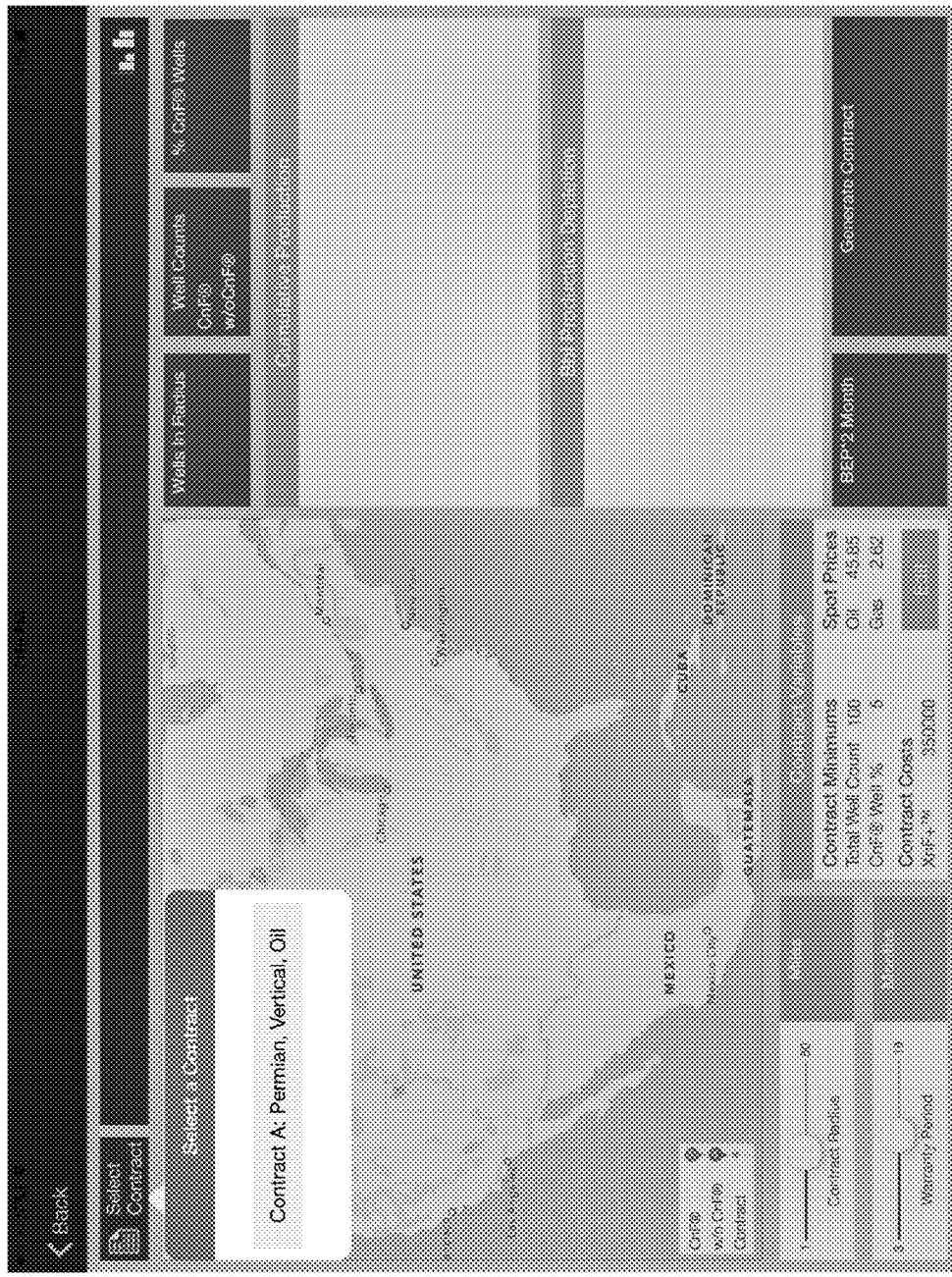

In FIG. 40, a view of the primary data related to a series of wells to be drilled is shown. The data for these contract wells, generally, shows the longitude and latitude of each well along with key projected data of the wells as usually or customarily defined by the operator/driller/owner of the well. FIG. 41 shows a further granularity and specificity of the projected production data for each individual well. These data inputs may vary by operator, well formation, geographic area, regulatory considerations and/or other factors.

Figure 42:
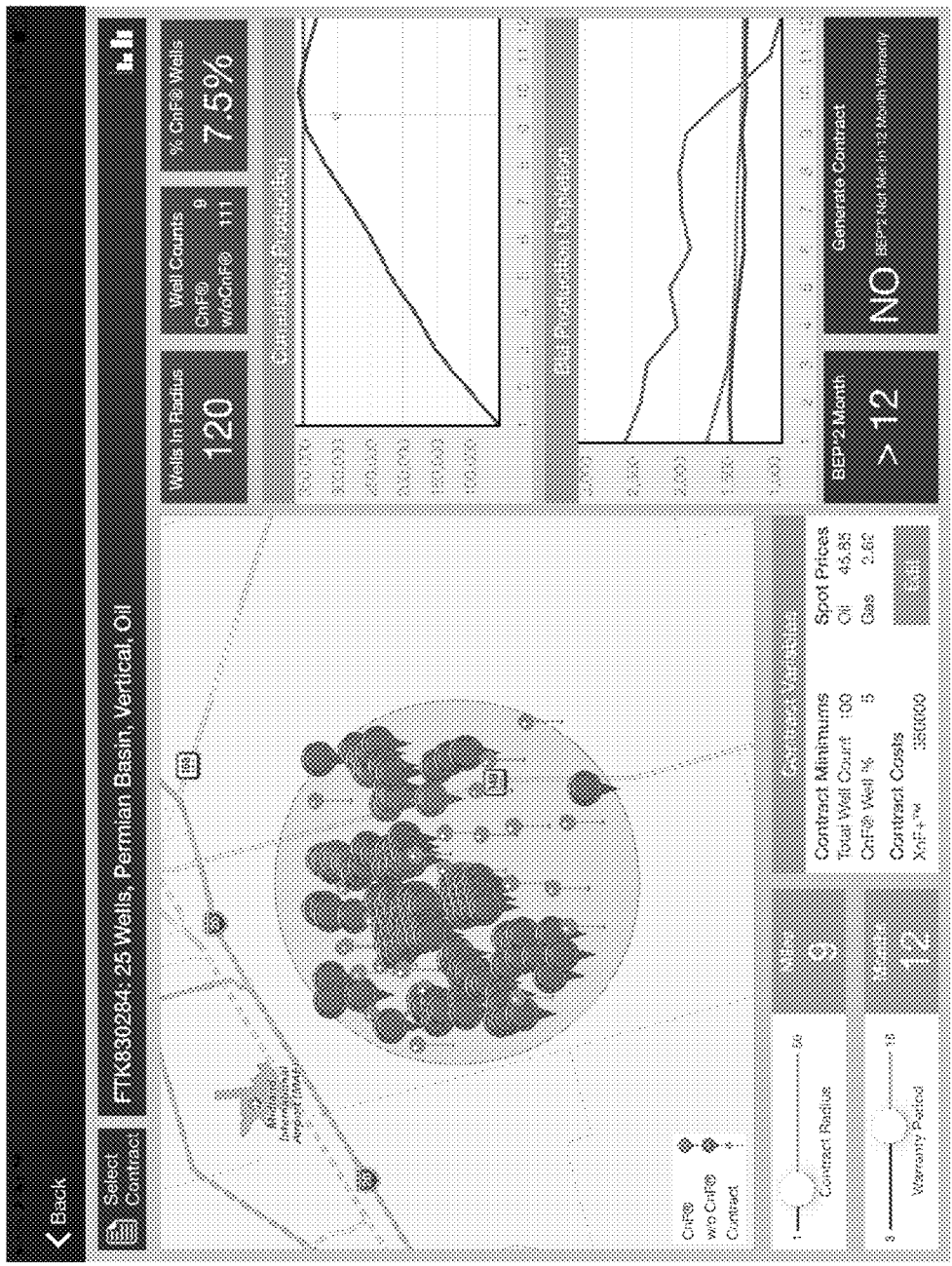

As shown in FIG. 42, the primary view is a map view, which is accessed through the "Production Warranty" tab in the main menu. As shown in the upper left hand corner, there is a drop down menu for selecting a potential contract for the warranty of one or more projected wells to be drilled. Note that there is a choice between choosing the Contract Radius to choose the area of historical wells containing the product to be warranted and the wells that did not historically contain that product. There is also a choice, including along a sliding scale, the period over which the efficacy product is evaluated. In the illustration shown, it is from 12 months to 18 months.

The historical data may also be provided as projected data based on reservoir modeling. While the examples provided hereinabove are primarily related to fracturing fluids, more specifically CNF fluid, projected reservoir data points may be relevant, specifically related to the secondary and tertiary recovery.

Figure 43:
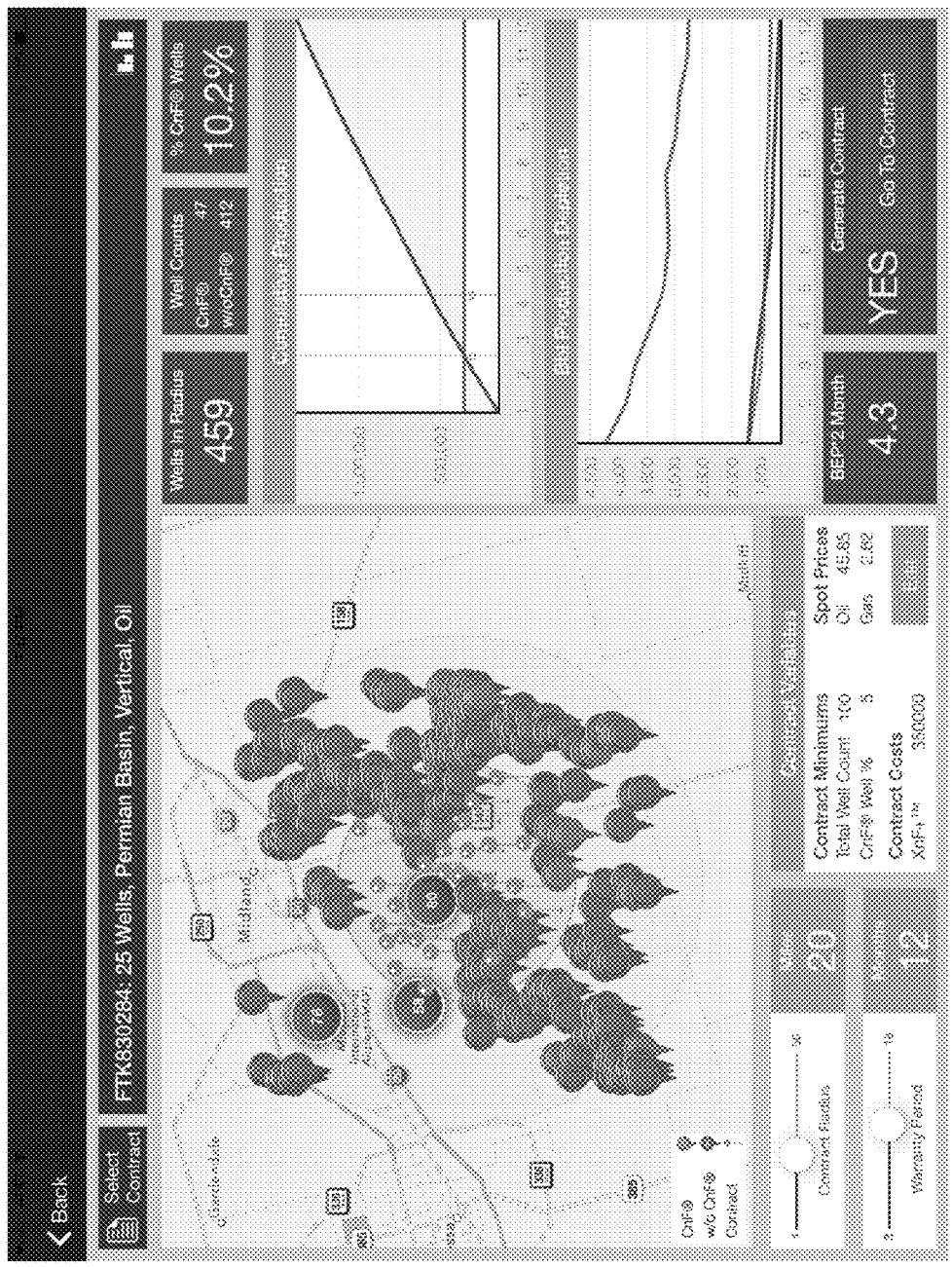

Once the contract is chosen, FIG. 43 shows a graphical representation of the radius of the wells to be drilled, initial default or predefined radius of same, warranty period. Key data, as shown in the upper right hand corner is dynamic as the various parameters are varied. The efficacy over time is shown on a cumulative basis, in this example graphically. In addition, there is a cumulative difference between the non-CNF (in this example) historical wells and the historical CNF (in this example) wells.

Not shown in the graphical examples shown, there are varying calculations taking into account factors such as a minimum number of different types of wells, taking into account "outlier" negative or positive performers, and the like.

Note that the screen will generally give an indication on whether the efficacy requirements have been met. As shown in the bottom right hand corner of FIG. 43, a message indicates that a contract cannot be generated because one or more criteria were not met where those criteria are required in the underwriting formula. In a preferred embodiment, a "NO" is generated and the user may not progress to accepting a contract.

Figure 44:
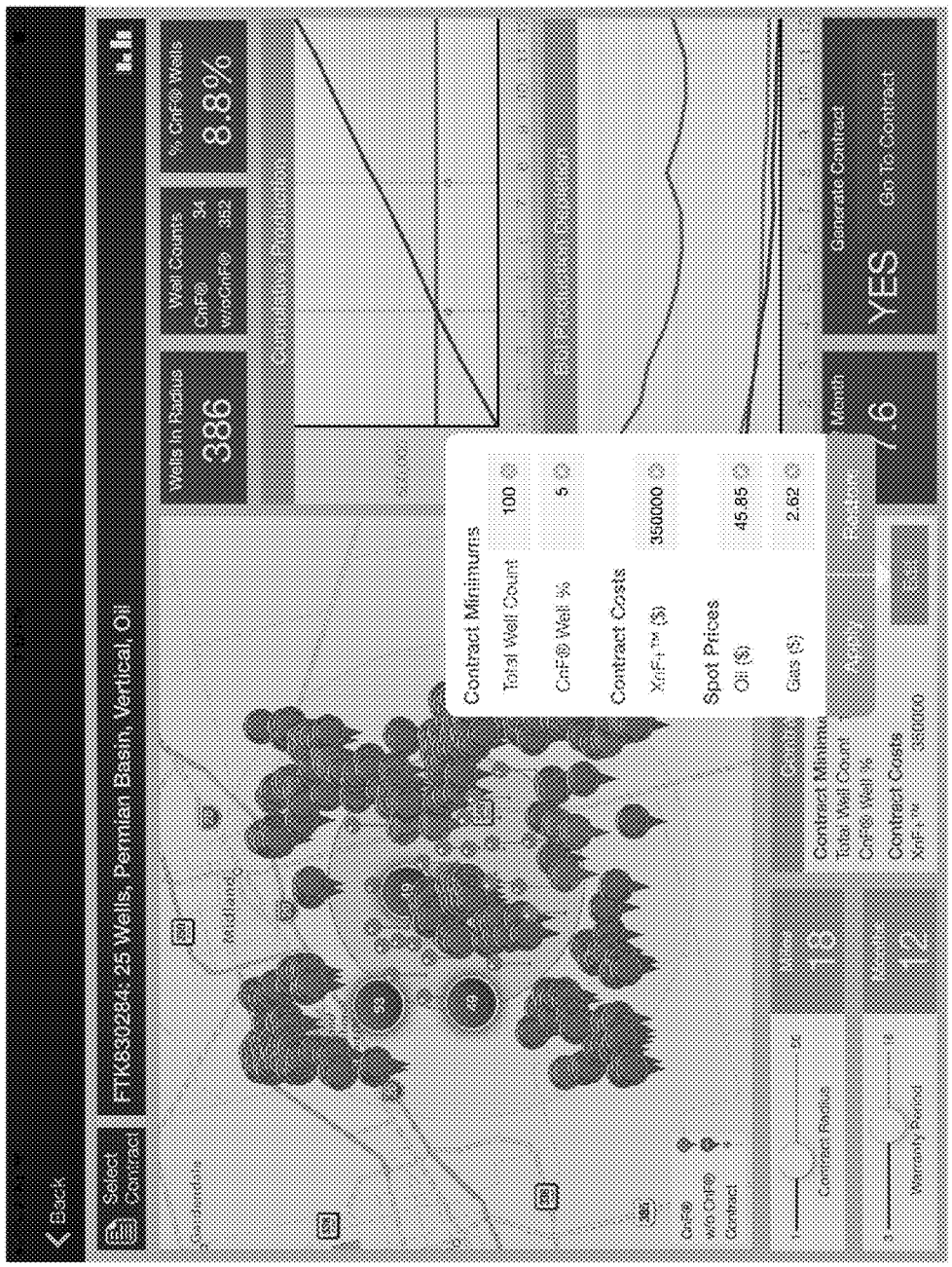

In FIG. 44, the radius of the wells to be considered is increased to 20 miles. This removes the prior negative indication on accepting a contract for efficacy. Note that, in the preferred embodiment, the screen shows a "YES" and a tab that allows a user to progress to final contract terms.

Figure 45:
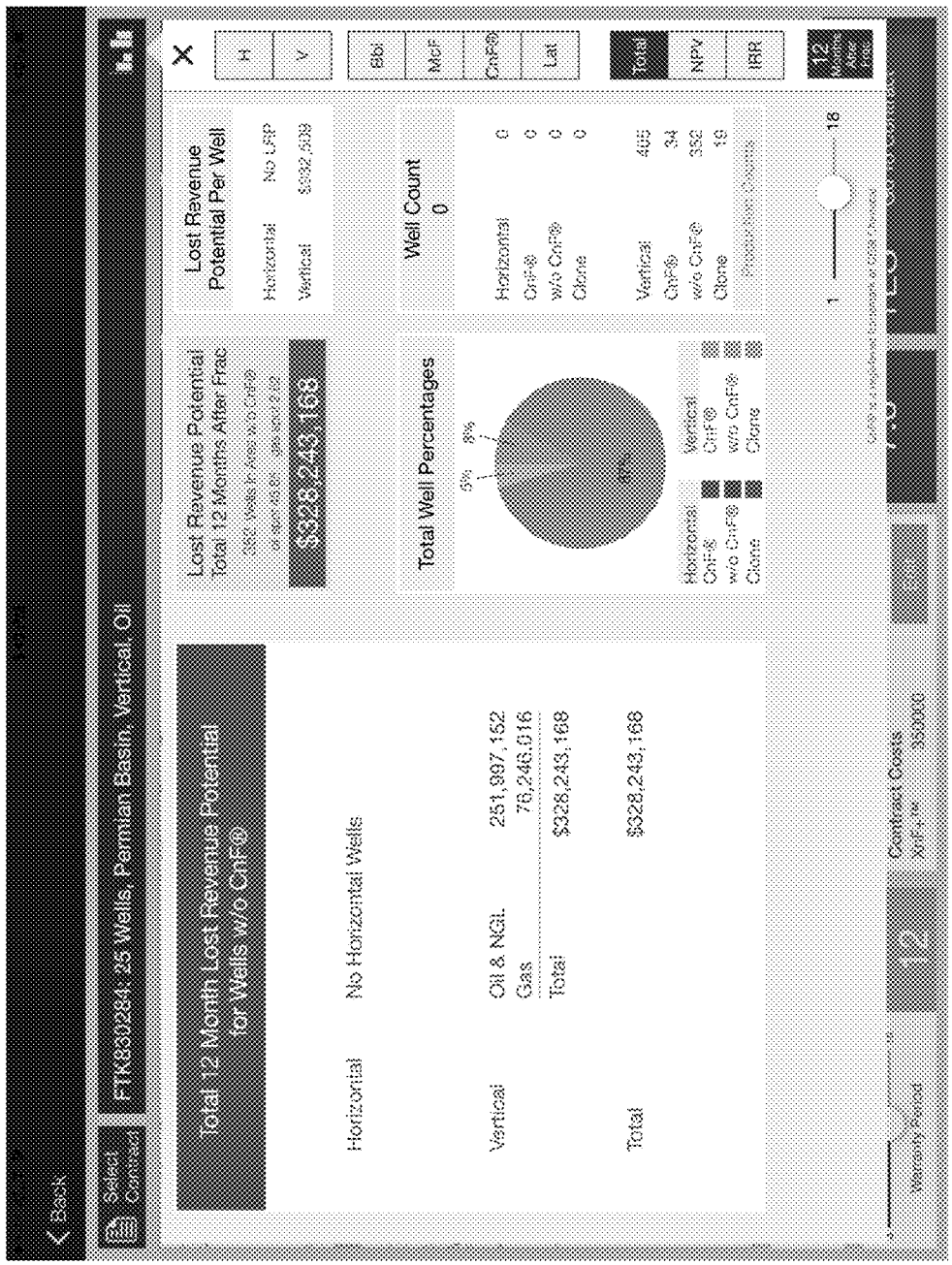

Note also, that in FIG. 45, the contract variables are also a part of the underwriting analysis. These include contract minimums, the cost of the contract including potentially the cost of the product warranted. It also includes other commercial variables outside of the terms of the contract such as the price of the produced material (e.g., the price of West Texas Intermediate).

In FIG. 45, all of the analysis above can be compared to the projected production values generally shown in the basic analysis.

In a particular underwriting scenario, well comparisons are done for (A) planned wells, (b) historical CnF® microemulsion-using wells, (c) historical wells without CnF® microemulsion use (for comparison purposes only), and (d): Increasing or Decreasing Radius as Required. A well depletion curve comparison might be done between (a) planned production over time of the "A" wells that is expected without the CnF+™ microemulsion use, (b) production over time of the "B" wells, historical data of wells with CnF® microemulsion use, and (c) production over time of the "C" wells, historical data of wells without CnF® microemulsion use. The cumulative difference over time between depletion curves might show (1) cost of CnF+™ microemulsion use, (2) cumulative difference of B-A over time, and (3) a breakeven point.

In an underwriter example of a loss scenario, assume 25 wells, contiguous, heterogeneous, and with a well plan from an operator with a $350K per well cost for CnF+™ microemulsion use. The complete cost of application would include warranty prices and terms and conditions. In one example, actual production data reported to the Texas Railroad Commission (for Texas wells) or other state agencies in other states, which contains a high degree of integrity in reported data, versus a CnF+™ microemulsion use projected production curve would illustrate a breakeven point and allow for a loss analysis. That loss can be mitigated through the use of a microemulsion associated with the warranty.

Research

Currently, laboratory data is limited to producing small-scale replications of the complex chemical interactions of the various fluids injected into the well and surrounding area for various purposes during the drilling and completion of an oil or gas well. The ability to compile the production data from a given basin under similar conditions and observe the difference in production data when a certain chemical is used, the effect of other chemicals and other technical variables related to the oil and gas well are taken into account.

In particular, it has been discovered that the overall production of oil and/or gas using CnF® microemulsion is superior to when the CnF® microemulsion are not utilized under similar circumstances, thus validating the research data from the laboratory and enhancing the overall knowledge and understanding of the efficacy of the use of CnF® microemulsion, and quantifying the probable success of the CnF® microemulsion under similar technical and geological conditions.

Sales and Marketing

As the efficacy of an additive such as a CnF® microemulsion is indicated by the data above, it is readily accessible to the sales and marketing force of an organization. A salesperson may sit down with a client at any level of an oil and gas company, detail the area around the particular area in question, and show the historical use of the chemical additive such as a CnF® microemulsion across a geographically relevant scope of existing wells to show the efficacy of using the product in the future. Note that due to the flexibility of the scope in which the data can be presented, the data may be presented to a customer at the enterprise level between high-level management all the way down to the field level to a specific application in a given oil or gas producing area.

Regulatory Applications

Federal and State agencies may also use the data to optimize tax revenues among by other activities, encouraging those producing/extracting its oil and gas assets to use best practices as it relates its drilling and completion of oil and gas wells, in particular to the chemicals that optimize production and thereby tax revenues. For example, with the use of a CnF® microemulsion, additional production in the near term and over the life of a given oil or gas well will generally be greater. Because of the flexibility of the system outlined above, the agency can determine to what extent and in what areas to best encourage certain best practices on a statewide or more granular basis, e.g., as to a given producing region.

Other Uses

It is understood that the same comparisons may be made in the highly regulated health care business, in the environmental area and even as it relates to climate studies. Applications to all of the these fields would also apply as it relates to insurance underwriting and risk management, financial market analysis, and political risk and supply chain risk As has now been described, a computer system can obtain and gather chemical composition data from one source, jurisdictional production data from another source, normalize and process that integrated data to derive well-to-well comparisons as a function of chemical composition used.

In addition to data processing, the present invention might include processes for carrying out actions based on that data processing, such as performing data processing steps described herein, then identifying suitable wells, purchasing those wells, and restarting drilling on those wells using a CnF® microemulsion.

While the systems and processes of the present invention have been described as encompassing numerous features, capabilities, architectures, and configurations, and depicted in detail for a mobile-based embodiment, it is to be appreciated that the process of the present invention encompasses any and all combinations of these and comparable embodiments and is not to be construed as being limited to any preferred embodiment, or the MBE specified in detail herein. Additionally, modifications may be made to the process flow, techniques, equipment used, or any other element, factor, or step without departing from the scope of the present invention.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

What is claimed is:

1. A method of displaying an efficacy of a particular chemical composition on a graphical user interface displayable by a computer display, the method comprising:
    displaying, by a computer system, selectable annotations representing a plurality of wells at a plurality of drilling sites on the graphical user interface, each of the selectable annotations representing a different corresponding one of the plurality of wells;
    displaying, by the computer system, a selectable user input associated with the particular chemical composition on the graphical user interface along with the selectable annotations;
    when a particular annotation of the selectable annotations has been selected, displaying, by the computer system, information about the well corresponding to the particular annotation on the graphical user interface, the information comprising one or both of chemical composition data and well yield data for the well corresponding to the particular annotation, the chemical composition data indicating which chemical compositions were injected into the well corresponding to the selectable annotation;
    identifying, by the computer system, first and second portions of the plurality of wells, the first portion of the plurality of wells having been injected with the particular chemical composition, the second portion of the plurality of wells having not been injected with the particular chemical composition;
    calculating, by the computer system, first and second values when the selectable user input is selected, the first value being associated with injecting the particular chemical composition into the first portion, the second value being associated with not injecting the particular chemical composition into the second portion; and
    displaying the first and second values by the computer system, the first and second values indicating the efficacy of injecting the particular chemical composition, and showing an improvement in a yield of the first portion of the plurality of wells when compared to the second portion of the plurality of wells.

2. The method of claim 1, wherein the information comprises both the chemical composition data and the well yield data for the well corresponding to the particular annotation, and
    the method further comprises matching, by the computer system, the chemical composition data for the well corresponding to the particular annotation with the well yield data for the well corresponding to the particular annotation by matching different ones of the plurality of drilling sites based on drill site parameters.

3. The method of claim 2, wherein the drill site parameters include geographic location.

4. The method of claim 2, wherein the drill site parameters include geologic characteristics.

5. The method of claim 1, further comprising:
    providing hydraulic fluids with the particular chemical composition to at least one well of the second portion of the plurality of wells.

6. The method of claim 1, further comprising:
    displaying, by the computer system, whether to use the particular chemical composition at a particular drilling site in the plurality of drilling sites based on the efficacy of injecting the particular chemical composition.

7. The method of claim 1, further comprising:
    displaying, by the computer system, whether to use the particular chemical composition at a particular drilling site that is distinct from the plurality of drilling sites based on the efficacy of injecting the particular chemical composition and well yield data obtained for the particular drilling site.

8. The method of claim 1, wherein a prior chemical composition used in a particular well of the second portion of the plurality of wells is distinct from the particular chemical composition, and the particular chemical composition is optimized to recover oil and/or gas from the particular well.

9. The method of claim 1, wherein the selectable annotations are displayed on a map.

10. The method of claim 9, further comprising:
    displaying, by the computer system, a user input configured to receive a radius from a user after the particular annotation has been selected; and
    displaying, by the computer system, only those of the plurality of wells within the radius of the well corresponding to the particular annotation on the map.

11. The method of claim 1, wherein the information displayed when the particular annotation has been selected comprises detail chemical data and monthly production data about the well corresponding to the particular annotation.

12. The method of claim 1, wherein the first value comprises a first net present value, and the second value comprises a second net present value.

13. The method of claim 1, wherein the the first and second values are displayed on a depletion line chart.

14. The method of claim 1, further comprising:

displaying, by the computer system, at least one of a lost revenue potential or a total lost revenue for the second portion not injected with the particular chemical composition.

15. The method of claim 1, wherein each of the selectable annotations displays a well direction of the well corresponding to the selectable annotation.

16. The method of claim 1, wherein each of the selectable annotations displays whether the well corresponding to the selectable annotation yields oil or gas.

17. The method of claim 1, wherein the computer system displays the chemical composition data and the well yield data for the particular annotation when the particular annotation has been selected.

18. The method of claim 17, wherein the chemical composition data displayed for the well corresponding to the particular annotation is normalized over the plurality of drilling sites, and the well yield data displayed for the well corresponding to the particular annotation is normalized over the plurality of drilling sites.

19. The method of claim 1, wherein the first value comprises a first internal rate of return, and the second value comprises a second internal rate of return.

20. A method of displaying an efficacy of a particular material on a graphical user interface displayable by a computer display, the method comprising:

displaying, by a computer system, selectable annotations representing a plurality of operational units, each of the selectable annotations representing a different corresponding one of the plurality of operational units;

displaying, by the computer system, a selectable user input associated with the particular material on the graphical user interface along with the selectable annotations;

when a particular annotation of the selectable annotations has been selected, displaying, by the computer system, information about the operational unit corresponding to the particular annotation on the graphical user interface, the information comprising one or both of first operational data and second operational data for the particular annotation, the first operational data indicating which materials were used at the operational unit corresponding to the selectable annotation;

identifying, by the computer system, first and second portions of the plurality of operational units, the particular material having been used at the first portion and the particular material not having been used at the second portion;

calculating, by the computer system, first and second values when the selectable user input is selected, the first value being associated with the particular material having been used at the first portion, the second value being associated with the particular material not having been used at the second portion; and displaying the first and second values by the computer system, the first and second values indicating the efficacy of using the particular material, and showing an improvement in the first portion of the plurality of operational units when compared to the second portion of the plurality of operational units.

* * * * *